(12) United States Patent
Shi et al.

(10) Patent No.: US 11,413,286 B2
(45) Date of Patent: Aug. 16, 2022

(54) PRODUCING ASTROCYTES USING SMALL MOLECULES

(71) Applicant: CITY OF HOPE, Duarte, CA (US)

(72) Inventors: Yanhong Shi, Arcadia, CA (US); E. Tian, Monrovia, CA (US)

(73) Assignee: CITY OF HOPE, Duarte, CA (US)

( * ) Notice: Subject to any disclaimer, the term of this patent is extended or adjusted under 35 U.S.C. 154(b) by 451 days.

(21) Appl. No.: 16/311,965

(22) PCT Filed: Jun. 21, 2017

(86) PCT No.: PCT/US2017/038611
§ 371 (c)(1),
(2) Date: Dec. 20, 2018

(87) PCT Pub. No.: WO2017/223241
PCT Pub. Date: Dec. 28, 2017

(65) Prior Publication Data
US 2019/0175597 A1 Jun. 13, 2019

Related U.S. Application Data

(60) Provisional application No. 62/353,214, filed on Jun. 22, 2016.

(51) Int. Cl.
| | | |
|---|---|---|
| *A61K 31/506* | (2006.01) | |
| *A61K 31/135* | (2006.01) | |
| *A61K 31/19* | (2006.01) | |
| *A61K 31/437* | (2006.01) | |
| *A61K 31/4439* | (2006.01) | |
| *A61K 31/444* | (2006.01) | |
| *A61K 35/30* | (2015.01) | |
| *A61K 38/18* | (2006.01) | |
| *A61P 25/28* | (2006.01) | |
| *C12N 5/079* | (2010.01) | |

(52) U.S. Cl.
CPC .......... *A61K 31/506* (2013.01); *A61K 31/135* (2013.01); *A61K 31/19* (2013.01); *A61K 31/437* (2013.01); *A61K 31/444* (2013.01); *A61K 31/4439* (2013.01); *A61K 35/30* (2013.01); *A61K 38/18* (2013.01); *A61P 25/28* (2018.01); *C12N 5/0622* (2013.01); *C12N 2501/01* (2013.01); *C12N 2501/065* (2013.01); *C12N 2501/115* (2013.01); *C12N 2501/15* (2013.01); *C12N 2501/603* (2013.01); *C12N 2501/727* (2013.01); *C12N 2501/999* (2013.01); *C12N 2506/1307* (2013.01)

(58) Field of Classification Search
CPC .... A61K 31/506; A61K 31/135; A61K 31/19; A61K 31/437; A61K 31/4439; A61K 31/444; A61K 35/30; A61K 38/18; A61P 25/28; C12N 5/0622
See application file for complete search history.

(56) References Cited

U.S. PATENT DOCUMENTS

| | | | | |
|---|---|---|---|---|
| 2013/0022583 | A1* | 1/2013 | Wernig | A61P 25/18 424/93.7 |
| 2013/0130387 | A1* | 5/2013 | Itskovitz-Eldor | A61P 43/00 435/456 |
| 2014/0120621 | A1 | 5/2014 | Hochedlinger et al. | |
| 2015/0250824 | A1* | 9/2015 | Ma | A61K 35/34 424/93.7 |
| 2015/0284681 | A1 | 10/2015 | Wernig et al. | |
| 2015/0353888 | A1* | 12/2015 | Inoue | C12N 5/0623 435/347 |
| 2019/0010451 | A1* | 1/2019 | Zhang | C12N 5/0619 |

OTHER PUBLICATIONS

Li et al., "Identification of Oct4-activating compounds that enhance reprogramming efficiency," PNAS, Dec. 18, 2012.*
Krencik et al., "Specification of transplantable astroglial subtypes from human pluripotent stem cells," Nature Biotechnology, vol. 29, No. 6, Jun. 2011.*
Bachetti, T., et al. (2008). "Mild functional effects of a novel GFAP mutant allele identified in a familial case of adult-onset Alexander disease" Eur J Hum Genet 16, 462-470.
Bachetti, T. et al. (2010). "In vitro treatments with ceftriaxone promote elimination of mutant glial fibrillary acidic protein and transcription downregulation" Experimental cell research 316, 2152-2165.
Banker, G.A. (1980). "Trophic interactions between astroglial cells and hippocampal neurons in culture" Science (New York, NY 209, 809-810.
Barres, B.A. (2008). "The mystery and magic of glia: a perspective on their roles in health and disease" Neuron 60, 430-440.
Bonaguidi, M.A., et al. (2005). "LIF and BMP signaling generate separate and discrete types of GFAP-expressing cells" Development (Cambridge, England) 132, 5503-5514.
Caiazzo, M., et al. (2011). "Direct generation of functional dopaminergic neurons from mouse and human fibroblasts" Nature 476, 224-227.
Caiazzo, M., et al. (2015). "Direct Conversion of Fibroblasts into Functional Astrocytes by Defined Transcription Factors" Stem Cell Reports 4, 25-36.
Calone, I., et al. (2012). "Inhibition of TGFβ signaling and its Implications in Anticancer Treatments" Exp. Oncol. 34, 9-16.
Cassady, J.P., et al. (2014). "Direct lineage conversion of adult mouse liver cells and B Tymphocytes to neural stem cells" Stem Cell Reports 3, 948-956.

(Continued)

*Primary Examiner* — Jared Barsky
(74) *Attorney, Agent, or Firm* — Perkins Coie LLP; Lara J. Dueppen; Yang Tang

(57) ABSTRACT

Disclosed herein are methods of reprograming autologous tissues or cells into astrocytes or astroglial progenitor cells using one or more small molecule compounds only without any transgenes. Also disclosed are methods of preventing or treating neurodegenerative diseases or neurological disorders associated with dysfunction of astrocytes, such as Alzheimer's Disease, by transplanting the astrocytes or astroglial progenitor cells produced by the methods disclosed herein into the brain of a subject suffering from the neurodegenerative disease or neurological disorder.

5 Claims, 21 Drawing Sheets

Specification includes a Sequence Listing.

(56) References Cited

OTHER PUBLICATIONS

Chaundhry, F.A. et al. (1995). "Glutamate transporters in glial plasma membranes: highly differentiated localizations revealed by quantitative ultrastructural immunocytochemistry" Neuron 15, 711-720.
Cheng, L., et al. (2014). "Generation of neural progenitor cells by chemical cocktails and Hypoxia" Cell research 24, 665-679.
Davis, R.L., et al. (1987). "Expression of a single transfected cDNA converts fibroblasts to myoblasts" Cell 51, 987-1000.
Eroglu, C., et al. (2010). "Regulation of synaptic connectivity by glia" Nature 468, 223-231.
Gellibert, F., et al. (2004). "Identification of 1,5-naphthyridine derivatives as a novel series of potent and selective TGF-beta type I receptor inhibitors" Journal of medicinal chemistry 47, 4494-4506.
Gross, R.E., et al. (1996). "Bone morphogenetic proteins promote astroglial lineage commitment by mammalian subventricularzone progenitor cells" Neuron 17, 595-606.
Hagemann, T.L., et al. (2006). Alexander disease-associated glial fibrillary acidic protein mutations in mice induce Rosenthal fiber formation and a white matter stress response. J Neurosci 26, 11162-11173.
Hama, H., et al. (2004). "PKC signaling mediates global enhancement of excitatory synaptogenesis in neurons triggered by local contact with astrocytes" Neuron 41, 405-415.
Han, D.W., et al. (2012). "Direct reprogramming of fibroblasts into neural stem cells by defined factors" Cell stem cell 10, 465-472.
Hatada, I., et al. (2008). "Astrocyte-specific genes are generally demethylated in neural precursor cells prior to astrocytic differentiation" PloS one 3, e3189. 9 pages.
Hawley, R.G. (2008). "Does retroviral insertional mutagenesis play a role in the generation of induced pluripotent stem cells?" Mol Ther 16, 1354-1355.
Hou, P., et al. (2013). "Pluripotent stem cells induced from mouse somatic cells by smallmolecule compounds" Science 341, 651-654.
Hu, W., et al. (2015). "Direct Conversion of Normal and Alzheimer's Disease Human Fibroblasts into Neuronal Cells by Small Molecules" Cell stem cell 17, 204-212.
Ichida, J.K., et al. (2009). "A small-molecule inhibitor of tgf-Beta signaling replaces sox2 in reprogramming by inducing nanog" Cell Stem Cell 5, 491-503.
Inman, G.J., et al. (2002). "SB-431542 is a potent and specific inhibitor of transforming growth factor-beta superfamily type I activin receptor-like kinase (ALK) receptors ALK4, ALK5, and ALK7" Mol Pharmacol 62, 65-74.
Irizarry, R.A, et al. (2003). "Exploration, normalization, and summaries of high density oligonucleotide array probe level data" Biostatistics 4, 249-264.
Kim, J., et al. (2011). "Direct reprogramming of mouse fibroblasts to neural progenitors" Proceedings of the National Academy of Sciences of the United States of America 108, 7838-7843.
Kohyama, J., et al. (2010). "BMP-induced REST regulates the establishment and maintenance of astrocytic identity" The Journal of Cell Biology 189, 159-170.
Li, W., et al. (2012). "Identification of Oct4-activating compounds that enhance reprogramming efficiency" Proceedings of the National Academy of Sciences of the United States of America 109, 20853-20858.
Li, X., et al. (2015). "Small-Molecule-Driven Direct Reprogramming of Mouse Fibroblasts into Functional Neurons" Cell Stem Cell 17, 195-203.
Lin, T., et al. (2009). "A chemical platform for improved induction of human iPSCs" Nature Methods 6, 805-808.
Lujan, E., et al. (2012). "Direct conversion of mouse fibroblasts to self-renewing, tripotent neural precursor cells" Proceedings of the National Academy of Sciences of the United States of America 109, 2527-2532.

Maherali, N., et al. (2009). "Tgfbeta signal inhibition cooperates in the induction of iPSCs and replaces Sox2 and cMyc" Curr Biol 19, 1718-1723.
Messing, A., et al. (2012). "Alexander Disease" J Neurosci 32, 5017-5023.
Molofsky, A.V., et al. (2012). "Astrocytes and disease: a neurodevelopmental perspective" Genes & development 26, 891-907.
Najm, F.J., et al. (2013). "Transcription factor-mediated reprogramming of fibroblasts to expandable, myelinogenic oligodendrocyte progenitor cells" Nature biotechnology 31, 426-433.
Okita, K., et al. (2008). "Generation of mouse induced pluripotent stem cells without viral vectors" Science 322, 949-953.
Pang, Z.P., et al. (2011). "Induction of human neuronal cells by defined transcription factors" Nature 476, 220-223.
Rajan, P., et al. (1998). "Multiple routes to astrocytic differentiation in the Cns" J Neurosci 18, 3620-3629.
Ring, K.L., et al. (2012). "Direct reprogramming of mouse and human fibroblasts into multipotent neural stem cells with a single factor" Cell stem cell 11, 100-109.
Schildge, S., et al. (2013). "Isolation and culture of mouse cortical astrocytes" J Vis Exp, 7 pages.
Simard, M., et al. (2004). "The neurobiology of glia in the context of water and ion homeostasis" Neuroscience 129, 877-896.
Smith, J.R., et al. (2008). "Inhibition of Activin/Nodal signaling promotes specification of human embryonic stem cells into neuroectoderm" Developmental biology 313, 107-117.
Sofroniew, M.V., et al. (2010). "Astrocytes: biology and pathology" Acta Neuropathologica 119, 7-35.
Song, H., et al. (2002). "Astroglia induce neurogenesis from adult neural stem cells" Nature 417, 39-44.
Szabo, P.E., et al. (2002). "Allele-specific expression of imprinted genes in mouse migratory primordial germ cells" Mechanisms of development 115, 157-160.
Takahashi, K., et al. (2006). "Induction of pluripotent stem cells from mouse embryonic and adult fibroblast cultures by defined factors" Cell 126, 663-676.
Thier, M., et al. (2012). "Direct conversion of fibroblasts into stably expandable neural stem cells" Cell stem cell 10, 473-479.
Tojo, M., et al. (2005). "The ALK-5 inhibitor A-83-01 inhibits Smad signaling and epithelial-to-mesenchymal transition by transforming growth factor-beta" Cancer Sci 96, 791-800.
Verkhratsky, A, et al. (2012). "Neurological diseases as primary gliopathies: A reassessment of neurocentrism" ASN neuro, 4, 131-149.
Vierbuchen, T., et al. (2010). "Direct conversion of fibroblasts to functional neurons by defined factors" Nature 463, 1035-1041.
Wang, D.D., et al. (2008). "The astrocyte odyssey" Progress in Neurobiology 86, 342-367.
Xu, R.H., et al. (2008). "NANOG is a direct target of TGFbeta/activin-mediated SMAD signaling in human ESCs" Cell Stem Cell 3, 196-206.
Yang, N., et al. (2013). "Generation of oligodendroglial cells by direct lineage conversion" Nature biotechnology 31, 434-439.
Yoo, A.S., et al. (2011). "MicroRNA-mediated conversion of human fibroblasts to neurons" Nature 476, 228-231.
Zhang, L., et al. (2015). "Small Molecules Efficiently Reprogram Human Astroglial Cells into Functional Neurons" Cell Stem Cell 17, 735-747.
Zhuo, L., et al. (1997). "Live astrocytes visualized by green fluorescent protein in transgenic mice" Developmental Biology 187, 36-42.
International Searching Authority, International Search Report and Written Opinion for International Application No. PCT/US17/38611. 10 pages.
International Searching Authority, International Preliminary Report on Patentability for International Application No. PCT/US17/38611.8 pages.

\* cited by examiner

G

H

I

J

PRODUCING ASTROCYTES USING SMALL MOLECULES

PRIORITY CLAIM

This application claims priority to U.S. Application No. 62/353,214, entitled "Producing Astrocytes Using Small Molecules," filed Jun. 22, 2016, which is incorporated herein by reference in its entirety, as if fully set forth herein.

STATEMENT OF GOVERNMENT FUNDING

This invention was made with government support under grant number TR2-01832 and RB4-06277 awarded by California Institute for Regenerative Medicine.

BACKGROUND

Astrocytes are glial cells that are located in all regions of the brain (Molofsky et al., 2012; Verkhratsky et al., 2012). They have long been held as the supporting components in neural tissues (Wang and Bordey, 2008; Sofroniew and Vinters, 2010). However, over the past decades, increasing evidence has established a variety of essential functions for astrocytes in neural development and in the pathogenesis of neurological diseases (Verkhratsky et al., 2012). Astrocytes play a critical role in neuronal maturation, synapse formation and plasticity, and glutamate clearance to reduce excitotoxicity (Banker, 1980; Song et al., 2002; Hama et al., 2004; Eroglu and Barres, 2010). Astrocyte dysfunction contributes to many neurodegenerative diseases and is the direct cause for some neurological disorders (Molofsky et al., 2012; Verkhratsky et al., 2012), such as Alexander disease (AxD) (Messing et al., 2012). Despite increasing data revealing new roles for astrocytes, the knowledge on astrocytes remains largely behind what is known about their neuronal counterpart. There is a need in the field to provide functional astrocytes, preferably from autologous tissues or cells, for preventing or treating neurodegenerative diseases or conditions associated with astrocyte dysfunction. The technology and methods disclosed herein satisfy this need.

SUMMARY

In one aspect, this disclosure relates to a method of reprogramming or converting somatic tissue or cells into astrocytes or astroglial progenitor cells by contacting the somatic tissue or cells with one or more small molecules only without introducing any transgenes. In some embodiments, the somatic tissue or cells are autologous tissue or cells. The somatic tissue or cells that can be reprogrammed or converted include but are not limited to fibroblasts, urinary cells, blood cells, adipocytes, keratinocytes, and dental pulp cells. In some embodiments, at least one small molecule is a TGF-β inhibitor, including but not limited to TGF-β inhibitor 616452, A-83-01, SB-431542, SD-208, LY 2109761, GW 788388, LDN-212854, A 77-01, LY2157299, K02288, ML347, and SB-505124 hydrochloride.

In some embodiments, two or more small molecules are used. For example, a TGF-β inhibitor can be used in combination with one or more of a histone deacetylase inhibitor, a GSK3β inhibitor, a lysine specific histone demethylase 1 (LSD1) inhibitor, and an Oct4-activating compound. In some embodiments, one or more small molecules include a combination of a histone deacetylase inhibitor VPA (V), a GSK3β inhibitor CHIR99021 (C), a TGF-β inhibitor 616452 (6), A-83-01 (A), or SB-431542 (S), a lysine specific histone demethylase 1 (LSD1) inhibitor tranylcypromine (T), and an Oct4-activating compound OAC1 (O). In some embodiments, the combination of the small molecules is "VC6TO" "VCATO" or "VCSTO," which includes the compounds disclosed herein. In a preferred embodiment, the combination comprises at least one small molecule that is a TGF-β inhibitor.

In another aspect, this disclosure relates to a method of preventing or treating a neurodegenerative disease or a neurological disorder associated with astrocyte dysfunction in a subject. The method entails reprogramming or converting somatic tissue or cells into astrocytes or astroglial progenitor cells by contacting the somatic tissue or cells with one or more small molecule compounds as disclosed herein, and transplanting the astrocytes or astroglial progenitor cells into the brain of the subject suffering from the neurodegenerative disease or neurological disorder. The neurodegenerative diseases or neurological disorders associated with astrocyte dysfunction include, for example, Alzheimer's disease, Alexander disease, Parkinson's disease, Huntington disease, amyotrophic lateral sclerosis (ALS), multiple sclerosis (MS), epilepsy, stroke and cerebral ischemia.

In a related aspect, this disclosure relates to a combination of small molecule compounds which induces or promotes reprogramming or converting somatic tissue or cells into astrocytes or astroglial progenitor cells. In some embodiments, the small molecule is a TGF-β inhibitor, including but not limited to TGF-β inhibitor 616452, A-83-01, SB-431542, SD-208, LY 2109761, GW 788388, LDN-212854, A 77-01, LY2157299, K02288, ML347, and SB-505124 hydrochloride. In some embodiments, two or more small molecules are used. For example, a TGF-β inhibitor can be used in combination with one or more of a histone deacetylase inhibitor, a GSK3β inhibitor, a lysine specific histone demethylase 1 (LSD1) inhibitor, and an Oct4-activating compound. In some embodiments, one or more small molecules include a combination of a histone deacetylase inhibitor VPA (V), a GSK3β inhibitor CHIR99021 (C), a TGF-β inhibitor 616452 (6), SB-431542 (S), or A-83-01 (A), a lysine specific histone demethylase 1 (LSD1) inhibitor tranylcypromine (T), and an Oct4-activating compound OAC1. In some embodiments, the combination of the small molecules is "VC6TO" "VCATO" or "VCSTO," which includes the compounds disclosed herein. In a preferred embodiment, the combination comprises at least one small molecule that is a TGF-β inhibitor.

In yet another aspect, this disclosure relates to a composition comprising a combination of small molecules, wherein the combination induces or promotes reprogramming or converting somatic tissue or cells into astrocytes or astroglial progenitor cells. In some embodiments, the small molecule is a TGF-β inhibitor, including but not limited to TGF-β inhibitor 616452, A-83-01, SB-431542, SD-208, LY 2109761, GW 788388, LDN-212854, A 77-01, LY2157299, K02288, ML347, and SB-505124 hydrochloride. In some embodiments, two or more small molecules are used. For example, a TGF-β inhibitor can be used in combination with one or more of a histone deacetylase inhibitor, a GSK3β inhibitor, a lysine specific histone demethylase 1 (LSD1) inhibitor, and an Oct4-activating compound. In some embodiments, one or more small molecules include a combination of a histone deacetylase inhibitor VPA (V), a GSK3β inhibitor CHIR99021 (C), a TGF-β inhibitor 616452 (6), SB-431542 (S), or A-83-01 (A), a lysine specific histone demethylase 1 (LSD1) inhibitor tranylcypromine (T), and an Oct4-activating compound OAC1. In some embodiments, the combination of the small molecules is "VC6TO" "VCATO" or "VCSTO," which includes the compounds disclosed herein. In a preferred embodiment, the combination comprises at least one small molecule that is a TGF-β inhibitor.

BRIEF DESCRIPTION OF THE DRAWINGS

This application contains at least one drawing executed in color. Copies of this application with color drawing(s) will be provided by the Office upon request and payment of the necessary fees.

FIG. 1A shows that VC6TO induced OG2 MEF into cells with astrocyte-like morphology. Oct4 promoter driven-GFP reporter fluorescence and phase contrast images of OG2 MEF before (D0) and after 25 days of VC6TO treatment (D25). No induction of Oct4-GFP reporter was detected. Arrows indicate astrocyte-like cells. Scale bar: 100 μm. FIG. 1B shows no contamination of neural lineage cells in MEF preparation. MEFs were stained for neural progenitor markers SOX1 and PAX6, neuronal markers TUJ1 and MAP2, astrocytes markers GFAP and S100β, and oligodendrocyte progenitor cell markers NG2 and OLIG2. No staining with these markers was detected. Nuclei Dapi staining is shown in blue. Scale bar, 100 μm. FIG. 1C shows FACS analysis showing 99.6% Fsp1+ cells in MEF. For all quantifications in the figures (unless otherwise specified), error bars are sd of the mean, $*p<0.05$, $p<0.01$, $*p<0.001$.

FIG. 2A shows the scheme of MEF preparation. FIG. 2B shows the scheme of astrocytic reprogramming with compound treatment. MEFM: MEF medium; iAM: induced astrocyte medium; AM: astrocyte medium. FIG. 2C shows immunostaining for GFAP and S100β in cells derived from MEFs treated with DMSO or VC6TO for 25 days. Nuclei were counter-stained with Dapi. Scale bar, 100 μm. FIGS. 2D and 2E show the percentage of GFAP-positive cells and GFAP and S100β-double positive cells from total cells. n=3,000 to 4,000 cells.

FIGS. 3A, 3C, 3E and 3G show immunostaining for GFAP in cells derived from MEFs treated with DMSO control or different compound combinations for 25 days. Nuclei were counter-stained with Dapi. Scale bar, 100 μm. FIGS. 3B, 3D, 3F, and 3H show the percentage of GFAP-positive cells in MEFs treated with individual compound combinations described in panels 3A, 3C, 3E, and 3G. n=2,000 to 6,000 cells.

FIG. 4A shows immunostaining for GFAP in cells reprogrammed from MEFs treated with VCSTO at different concentrations of S (SB-431542). Scale bar, 100 μm. FIG. 4B shows the percentage of GFAP-positive cells in MEFs treated with VCSTO at different concentrations of S. n=2,000 to 6,000 cells counted for each treatment group. FIG. 4C shows that treatment with VCSTO exerted no cellular toxicity. MEFs were treated with DMSO or VCSTO with increasing concentrations of S. Cell toxicity was determined by counting live cells 1 week or 2 weeks after vehicle or compound treatment. Error bars are sd of the mean. n=4 experimental repeats for each treatment group. FIG. 4D shows relative expression levels of TGFβ downstream target genes in MEFs treated with vehicle only or VCSTO compounds, measured by real time PCR. The expression in MEFs treated with vehicle control was defined as 1. n=3 experimental repeats.

FIG. 5A shows immunostaining for GFAP and S10β in cells generated from tail tip fibroblasts (TTFs) treated with VCSTO for 25 days. Nuclei Dapi staining is shown in blue in the merged image. Scale bar, 50 μm. FIGS. 5B and 5C show quantification of the percentage of GFAP-positive cells (5B) and GFAP and S100β-double positive cells (5C) in total Dapi-positive cells. For panels 5B and 5C, error bars are sd of the mean. $***p<0.001$. n=967 cells for TTF-DMSO, n=1118 cells for TTF-VCSTO.

FIGS. 6A-6C show immunostaining for GFAP and S100β (6A), GFAP and ALDH1L1 (6B), GFAP and visualizing GFAP-GFP (6C) in VCSTO-induced cells. Nuclei Dapi staining (blue) is included in the merged images. Scale bar, 50 μm. In panel 6C, MEF from GFAP-GFP mice were induced by VCSTO. FIG. 6D shows the expression of astrocyte-related genes in VCSTO-induced astrocytes (iA), relative to MEF, measured by real time PCR. The expression in MEF was defined as 1. n=3 experimental repeats. FIG. 6E shows bisulfite sequencing the Gfap promoter region in MEF, iA and mouse primary astrocytes (pA). Open and closed circles indicate unmethylated and methylated CpGs, respectively. FIG. 6F shows immunostaining for GFAP in cells treated with VCSTO for 10, 15, 20 and 25 days. Scale bar, 100 μm. FIG. 6G shows the percentage of GFAP-positive cells in cells treated with VCSTO for different days. FIG. 6H shows real time PCR of astrocyte markers at different days of VCSTO treatment. The expression at day 0 was defined as 1. n=3 experimental repeats. FIG. 6I shows RT-PCR of pluripotency markers, Oct4 and Nanog, and neural progenitor markers, Sox1 and Pax6, during the time course of VCSTO treatment. RNA from mouse embryonic stem cells (ESC) and neural progenitor cells (NPC) was included as positive controls.

FIG. 7A shows heatmap presentation of microarray analysis of MEFs, VCSTO-induced astrocytes (iA) and mouse primary astrocytes (pA). Genes upregulated in iA and pA, compared to MEFs, are shown in red, whereas genes downregulated in iA and pA, compared to MEFs, are shown in blue. In FIG. 7B, gene ontology (GO) terms for genes upregulated in both iA and pA, relative to MEFs, are shown in red, whereas GO terms associated with genes downregulated in iA and pA are shown in blue. The X axis represents enrichment scores, with p value calculated via Fisher's exact test. FIG. 7C shows heatmap presentation of a selected set of fibroblast-related genes (the upper 4 genes) and astrocyte-related genes (the lower 4 genes). FIGS. 7D and 7E show real time PCR validation of the expression of 4 fibroblast-associated genes (7D) and 4 astrocyte-associated genes (7E). The expression in MEFs was defined as 1. n=3 experimental repeats. FIG. 7F shows schematic presentation of different regions of the brain. FIG. 7G shows relative expression of regional subtype markers in iA measured by real time PCR. FB: forebrain; HB: hindbrain; DB: dorsal brain; VB: ventral brain. n=3 experimental repeats.

FIG. 8A shows hierarchical clustering of induced astrocytes (iA), primary astrocytes (pA) and MEF based on all the probe sets in microarray data. FIG. 8B shows Pearson's correlation analysis of iA, pA, and MEF. FIGS. 8C and 8D show RT-PCR analysis of 3 fibroblast genes (8C) and 3 astrocyte marker genes (8D) in MEF, iA and pA. The expression in MEF was defined as 1. FIG. 8E shows relative expression of regional subtype markers in iA measured by real time PCR. FB: forebrain; HB: hindbrain; DB: dorsal brain; VB: ventral brain. Error bars are sd of the mean. p<0.01, *p<0.001 by Student's t-test. n=3 experimental repeats.

FIG. 9A shows immunostaining mouse primary cortical neurons for Map2 and Synapsin after co-culturing with MEF, induced astrocytes (iA), and mouse primary astrocytes (pA) for 5 days. Scale bar, 50 µm. FIG. 9B shows quantification of Map2+neurite length in neurons co-cultured with MEF, iA and pA. n=1,000 cells. FIG. 9C shows increased Map2+Synapsin+ puncta in neurons co-cultured with iA and pA, relative to co-culture with MEF. Scale bar, 10 µm. FIG. 9D shows quantification of Map2+Synapsin+ puncta per 50 µm neurite length in neurons co-cultured with MEF, iA and pA. n=30 neurites. FIG. 9E shows measurement of glutamate uptake in iA, PA and MEF. n=3 experimental repeats. FIG. 9F shows calcium signal change in response to glutamate stimulation shown by calcium reporter fluorescent dye intensity change ($\Delta F/F_0$) over time (second, s) in iA. Scale bar, 100 µm. FIG. 9G shows lack of calcium spikes after glutamate stimulation in MEF. FIG. 9H shows calcium spikes after glutamate stimulation in pA. FIG. 9I shows quantification of $\Delta F/F0$ in MEF, iA and pA in response to glutamate stimulation. n=400 to 600 cells.

FIG. 11A shows timeline of cell transplantation and brain harvest. FIG. 11B shows two examples of GFP-labeled VCSTO-induced astrocytes (iA) in grafted brains that stained positive for both GFP and GFAP. The endogenous astrocytes are shown as GFP-negative but GFAP-positive. Scale bar, 25 µm. FIG. 11C shows higher magnification images of individual GFP and GFAP double positive cells that are indicated by arrows in panel b. Scale bar, 10 µm. FIG. 11D shows that MEF failed to survive in transplanted brains. MEF were labeled by GFP and transplanted into brains of neonatal immunodeficient mice. No GFP signal was detected in various regions of MEF-transplanted brains two weeks after transplantation. Scale bar, 25 µm.

FIG. 12A shows transfection of the R239C AxD mutant GFAP-GFP to iA induced GFAP protein aggregates and αB-crystallin expression. iA transfected with the WT and AxD GFAP-GFP were immunostained for GFAP and αB-crystallin. The transfected cells are indicated by GFP. Nuclei Dapi staining (blue) is included in the merged images. Scale bar, 10 µm. FIG. 12B shows that ceftriaxone treatment reduced GFAP protein aggregates in iA transfected with the AxD mutant GFAP-GFP. iA transfected with the AxD GFAP-GFP were treated with ceftriaxone (+Cef) or vehicle control (−Cef), and stained for GFAP and S100β. Scale bar, 10 µm. FIG. 12C shows that ceftriaxone treatment reduced GFAP protein aggregates in induced astrocytes (iA) transfected with the AxD mutant GFAP-GFP. The percentage of iA that contained the GFAP-GFP aggregates was reduced upon ceftriaxone treatment. n=400 to 500 cells. FIG. 12D shows that ceftriaxone treatment had no effect on GFAP protein aggregates in MEF. MEF transduced with the AxD GFAP-GFP were treated with ceftriaxone (+Cef) or vehicle control (−Cef). The percentage of MEF that contain the GFAP-GFP aggregates remained the same in the absence or presence of ceftriaxone treatment. n=600 to 900 cells. FIG. 12E shows reduced glutamate uptake in iA transduced with AxD mutant GFAP, compared to iA transduced with WT GFAP. n=3 experimental repeats. Error bars are sd of the mean, **p<0.01 by Student's t-test.

FIG. 13A shows immunostaining for S100β in cells derived from human fibroblasts (SCC058, for panels 13A to 13E) treated with DMSO or VCSTO. Nuclei were counter-stained with Dapi. Scale bar, 100 µm for panels 13A and 13B. FIG. 13B shows immunostaining for S100β or GFAP in cells derived from human fibroblasts treated with DMSO or VCSTO, followed by CNTF treatment. FIG. 13C shows the percentage of S100β-positive cells or GFAP-positive cells. n=3,000 to 4,000 cells. FIG. 13D show expression of astrocyte marker genes in VCSTO-induced human astrocytes (iA) as measured by real time PCR. The expression in human fibroblasts (hF) was defined as 1. n=4 experimental repeats. FIG. 13E shows substantially elevated glutamate uptake in iA relative to parental fibroblasts (hF). n=3 experimental repeats. FIG. 13F shows calcium imaging analysis of human induced astrocytes. Human induced astrocytes (iA) exhibited calcium signal change in response to glutamate stimulation, similar to human iPSC-derived astrocytes (hA). Lack of calcium spikes after glutamate stimulation in human fibroblasts (hF) was included as a negative control. FIG. 13G shows immunostaining for S100β and GFAP in cells derived from human adult fibroblasts (AG14048, for panels 13G to 13J) treated with DMSO or VCSTO. Nuclei were counter-stained with Dapi. Scale bar, 100 µm. FIG. 13H shows the percentage of S100β-positive cells or GFAP-positive cells. n=1,000 cells. FIG. 13I shows expression of astrocyte marker genes in iA relative to hF as measured by real time PCR. n=4 experimental repeats. FIG. 13J shows substantially elevated glutamate uptake in human iA relative to hF. n=3 experimental repeats.

DETAILED DESCRIPTION

Figure 1:
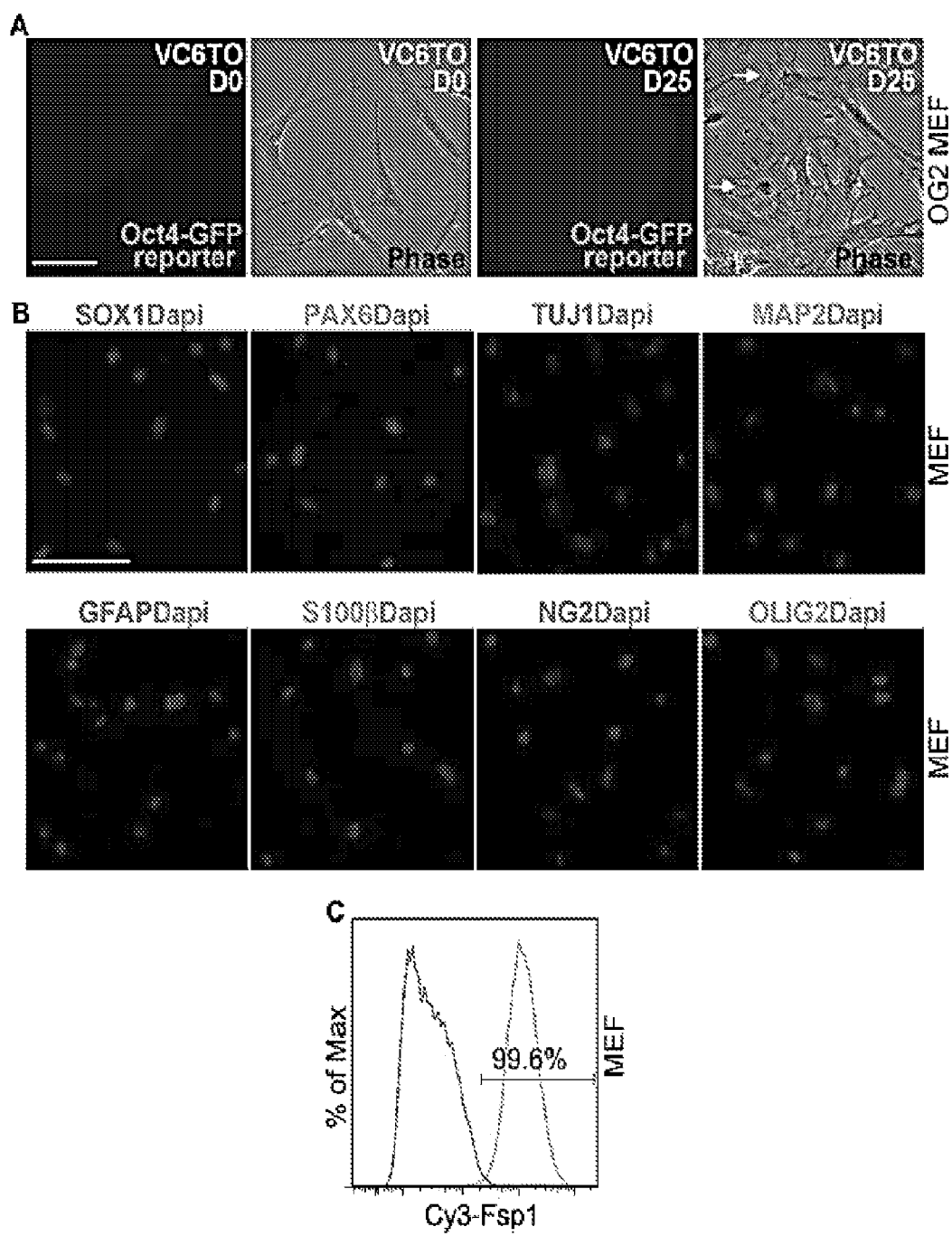
FIGS. 1A-1C illustrate direct reprogramming MEF into astrocyte-like cells.

The following description of the invention is merely intended to illustrate various embodiments of the invention. As such, the specific modifications discussed are not to be construed as limitations on the scope of the invention. It will be apparent to one skilled in the art that various equivalents, changes, and modifications may be made without departing from the scope of the invention, and it is understood that such equivalent embodiments are to be included herein.

Expression of lineage-specific factors has been shown to induce cell fate change, including reprogramming somatic cells to induced pluripotent stem cells (iPSCs) (Takahashi and Yamanaka, 2006) and converting one type of somatic cells to another (Davis et al., 1987). The latter is also called direct reprogramming or conversion. Extensive efforts have been devoted into converting somatic cells, like fibroblasts, into different types of neural cells, such as neural stem cells (Kim et al., 2011; Han et al., 2012; Lujan et al., 2012), neurons (Vierbuchen et al., 2010; Caiazzo et al., 2011; Pang et al., 2011; Yoo et al., 2011), and oligodendrocytes (Najm et al., 2013; Yang et al., 2013). Direct reprogramming of somatic cells into astrocytes using defined transcription factors has been reported (Caiazzo et al., 2015). However, the conventional technologies have certain restrictions. For example, the process of inducing human iPSCs from somatic cells such as fibroblasts and then converting human iPSCs to astrocytes is a lengthy process and takes about 90 days or even longer. Direct reprogramming of somatic cells into astrocytes using certain transcription factors involves introducing transgenes and therefore leaves "footprint" of residual transgenes or other contaminants.

Introducing exogenous factors in reprogramming has raised various concerns, including the risk of insertional mutagenesis and genetic alteration associated with retroviral delivery (Hawley, 2008), low reprogramming efficiency associated with episomal transfection (Okita et al., 2008). Cocktails of small molecules were shown to convert mouse or human fibroblasts into neurons (Hu et al., 2015; Li et al., 2015). However, no chemical reprogramming has been reported to change fibroblasts, or any other mature cell types, to astrocytes yet.

The technology and methods disclosed herein solves the problems in the art by direct reprogramming or converting somatic cells such as fibroblasts into astrocytes using one or more small molecules without the requirement of producing any intermediate stem cells and without introducing any transgene or contaminant. The process of direct reprogramming disclosed herein takes much shorter time, e.g., less than or about 30 days, than the conventional technology, e.g., 90 days.

As described in this disclosure, mouse or human fibroblasts were reprogrammed into functional astrocytes, which possess the ability to promote neuronal maturation and synaptic formation, uptake glutamate, and induce calcium signal in response to glutamate stimulation. Although rapid progress has been made in converting somatic cells into other types of neural cells, such as neural stem cells, neurons, and oligodendrocytes, direct reprogramming of somatic cells into astrocytes remains largely behind. Induced neurons can be developed into useful tools for modeling a variety of neurological diseases affecting neurons (Lujan and Wernig, 2012). However, induced neuronal cells would have limitations for modeling disease affecting astrocytes. Although astrocytes could be derived from iPSCs, the differentiation process is lengthy. These limitations could be overcome by inducing astrocytes directly from fibroblasts in a relatively short period of time as described in detail in this disclosure.

Disclosed herein is an example of pure chemical induction of lineage conversion from a mature somatic cell type to astrocytes. A previous study reported the derivation of iPSCs from mouse somatic cells using 6 small molecules VC6TFZ (Hou et al., 2013). Part of this compound cocktail, VC6 was used to convert somatic cells into neural progenitor cells under hypoxia (Cheng et al., 2014). In recent studies, different combinations of small molecules were used to convert somatic cells into neuronal cells (Hu et al., 2015; Li et al., 2015; Zhang et al., 2015). Disclosed herein is a method to reprogram mammalian fibroblasts into astrocytes using small molecule compounds only, without using any transgenes or viral transduction. Moreover, it was unexpectedly found that the TGFβ inhibitor alone was able to induce GFAP-positive cells from MEFs, providing an example that one single compound is able to induce the conversion of one somatic cell type to another.

Previous studies described ways to derive astrocytes from somatic cells by going through iPSC or iNSC/iNPC intermediates (Han et al., 2012; Lujan et al., 2012; Ring et al., 2012; Thier et al., 2012; Cassady et al., 2014). In these studies, astrocytes were derived from MEFs at an efficiency of 0.004% to 2% in up to 70 days. Disclosed herein is a direct reprogramming method that does not go through iPSC or iNSC/iNPC intermediate state. Astrocytes can be converted from MEFs at an efficiency of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, in a shorter period of time, such as 20 to 25 days, by the method disclosed herein. Therefore, the direct chemical reprogramming method described in this disclosure provides a more rapid and efficient way to derive astrocytes from fibroblasts.

As disclosed herein, the chemically induced astrocytes can be used to model diseases with astrocyte dysfunction. The working examples demonstrate that when an AxD mutant GFAP was transfected into induced astrocytes, the phenotype of GFAP protein aggregation observed in AxD patient astrocytes was recapitulated. Moreover, these protein aggregates were responsive to ceftriaxone treatment. Therefore, the chemically induced astrocytes disclosed herein can be used as a tool to study neurodevelopment in glial context, and to model a variety of neurological diseases with astrocyte dysfunction. Additionally, induced astrocytes containing disease-causing mutations can be produced by the methods disclosed herein. The induced astrocytes, as well as induced astrocytes containing mutations can be used for detecting, preventing or treating astrocyte-associated diseases.

In one aspect, disclosed herein is a method of reprogramming or converting somatic tissue or cells into astrocytes or astroglial progenitor cells using one or more small molecules only, without introducing any transgenes. In some embodiments, the somatic tissue or cells to be converted into astrocytes or astroglial progenitor cells are autologous tissue or cells. In some embodiments, the somatic tissue or cells that can be converted to astrocytes or astroglial progenitor cells include fibroblasts, urinary cells, blood cells, adipocytes, keratinocytes, and dental pulp cells.

The method includes contacting the somatic tissue or cells with one or more small molecules, wherein the one or more small molecules include at least one TGF-β inhibitor. In some embodiments, the TGF-β inhibitor is an inhibitor of TGF-βR1 (ALK5). The somatic tissue or cells are cultured in the presence of the one or more small molecules under a suitable condition for a period of time sufficient for the somatic tissue or cells to be converted into astrocytes or astroglial progenitor cells.

In some embodiments, a single small molecule is sufficient to induce the conversion to astrocytes or astroglial progenitor cells, and the small molecule is a TGF-β inhibitor. In other embodiments, two or more small molecules are used, and at least one small molecule is a TGF-β inhibitor.

Small molecule TGF-β inhibitors are known in the art (Calone 2012) and many are commercially available. Some examples of TGF-β inhibitors include but are not limited to 616452, A-83-01, SB-431542, SD-208, LY 2109761, GW 788388, LDN-212854, A 77-01, LY2157299, K02288, ML347, and SB-505124 hydrochloride, as shown in Table 1 below.

TABLE 1

| | TGF-β Inhibitors | |
|---|---|---|
| Small Molecule | Chemical Name | Chemical Structure |
| 616452 (Alk 5 Inhibitor II or RepSox) | 2-[5-(6-methylpyridin-2-yl)-1H-pyrazol-4-yl]-1,5-naphthyridine | |
| A-83-01 | 3-(6-methylpyridin-2-yl)-N-phenyl-4-quinolin-4-ylpyrazole-1-carbothioamide | |
| SB-431542 | 4-[4-(1,3-benzodioxol-5-yl)-5-pyridin-2-yl-1H-imidazol-2-yl]benzamide | |
| SD-208 | 2-(5-chloro-2-fluorophenyl)-N-pyridin-4-ylpteridin-4-amine | |
| LY 2109761 | 4-[2-[4-(2-pyridin-2-yl-5,6-dihydro-4H-pyrrolo[1,2-b]pyrazol-3-yl)quinolin-7-yl]oxyethyl]morpholine | |

TABLE 1-continued

TGF-β Inhibitors

| Small Molecule | Chemical Name | Chemical Structure |
|---|---|---|
| GW 788388 | N-(oxan-4-yl)-4-[4-(5-pyridin-2-yl-1H-pyrazol-4-yl)pyridin-2-yl]benzamide | 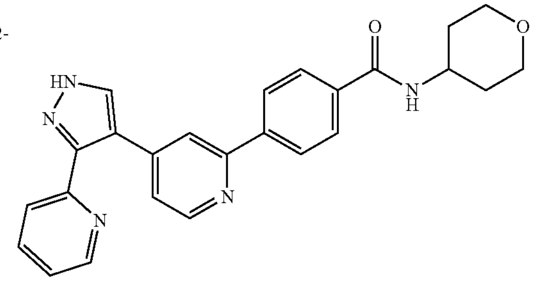 |
| LDN-212854 | 5-[6-[4-(1-Piperazinyl)phenyl]pyrazolo[1,5-a]pyrimidin-3-yl]quinoline | 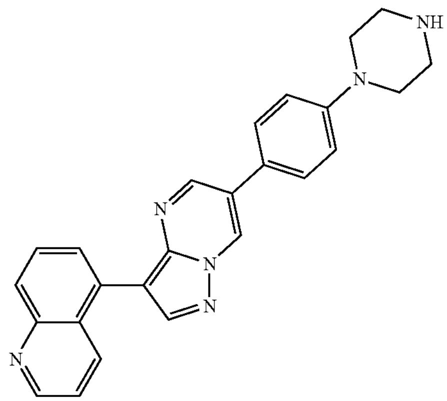 [SMILES: c1cc(-c2cnn3cc(-c4ccc(N5CCNCC5)cc4)cnc23)c2cccnc2c1] |
| A 77-01 | 4-[5-(6-methylpyridin-2-yl)-1H-pyrazol-4-yl]quinoline | 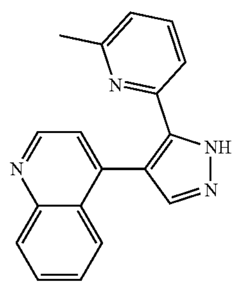 [SMILES: Cc1cccc(-c2[nH]ncc2-c2ccnc3ccccc23)n1] |
| LY2157299 | 4-[2-(6-methylpyridin-2-yl)-5,6-dihydro-4H-pyrrolo[1,2-b]pyrazol-3-yl]quinoline-6-carboxamide | 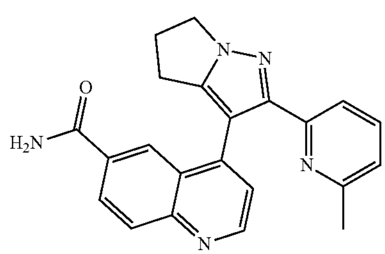 [SMILES: Cc1cccc(-c2nn3c(c2-c2ccnc4ccc(C(N)=O)cc24)CCC3)n1] |
| K02288 | 3-[6-amino-5-(3,4,5-trimethoxyphenyl)pyridin-3-yl]phenol | 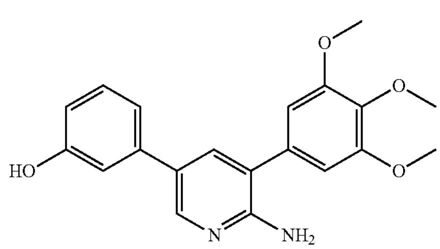 [SMILES: COc1cc(-c2cc(-c3cccc(O)c3)cnc2N)cc(OC)c1OC] |

TABLE 1-continued

| | TGF-β Inhibitors | |
|---|---|---|
| Small Molecule | Chemical Name | Chemical Structure |
| ML347 | 5-[6-(4-Methoxyphenyl)pyrazolo[1,5-a]pyrimidin-3-yl]quinoline | |
| SB-505124 hydrochloride | 2-[4-(1,3-benzodioxol-5-yl)-2-tert-butyl-1H-imidazol-5-yl]-6-methylpyridine | HCl |

In some embodiments, two or more small molecules are used. In combination with a TGF-β inhibitor, at least one of a histone deacetylase (HDAC) inhibitor, a GSK3β inhibitor, a lysine specific histone demethylase 1 (LSD1) inhibitor, and an Oct4-activating compound can be used. Some examples of each category are provided in the tables below.

TABLE 2

| HDAC Inhibitors | |
|---|---|
| Small Molecule | Chemical Structure |
| Trichostatin A | |
| Sodium butyrate | |
| Vorinostat | |

TABLE 3

GSK3β Inhibitors

| Small Molecule | Chemical Structure |
| --- | --- |
| GSK-3 Inhibitor IX | 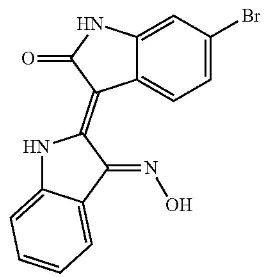 [SMILES: O=C1Nc2cc(Br)ccc2/C1=C1/Nc2ccccc2/C1=N\O] |
| Kenpaullone | 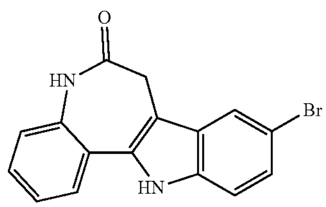 [SMILES: O=C1Cc2c([nH]c3ccc(Br)cc23)-c2ccccc2N1] |
| Lithium Chloride | Li⁺ Cl⁻ |
| GSK-3β Inhibitor XII | 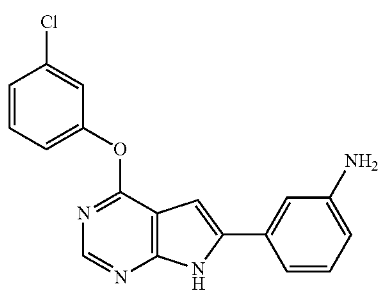 [SMILES: Nc1cccc(-c2cc3c(Oc4cccc(Cl)c4)ncnc3[nH]2)c1] |
| GSK-3 Inhibitor XVI | |
| 10Z-Hymenialdisine | 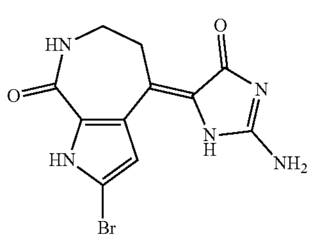 [SMILES: NC1=NC(=O)/C(=C2\CCNC(=O)c3[nH]c(Br)cc32)N1] |

TABLE 3-continued

GSK3β Inhibitors

| Small Molecule | Chemical Structure |
|---|---|
| CHIR-98014 | 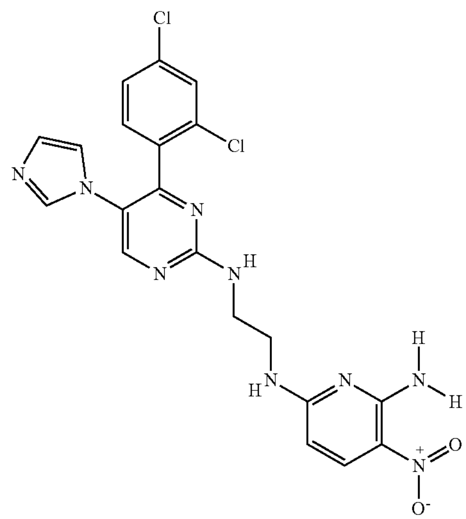 |
| GSK-3β Inhibitor VI | 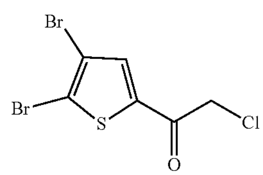 [SMILES: O=C(CCl)c1cc(Br)c(Br)s1] |
| GSK-3β Inhibitor I | 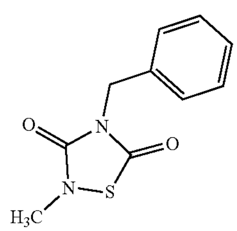 |
| GSK-3β Inhibitor VII | 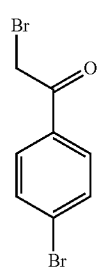 |
| 3F8 | 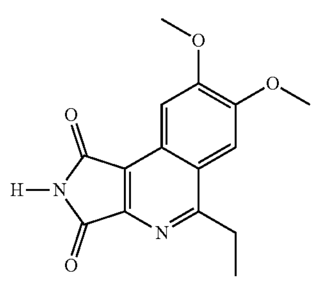 [SMILES: CCc1nc2c(c3cc(OC)c(OC)cc13)C(=O)NC2=O] |

TABLE 3-continued
| GSK3β Inhibitors | |
|---|---|
| Small Molecule | Chemical Structure |
| GSK-3 Inhibitor II | 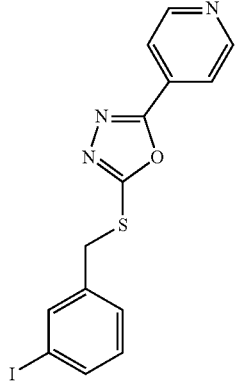 [SMILES: Ic1cccc(CSc2nnc(-c3ccncc3)o2)c1] |
| GSK-3β Inhibitor VIII | 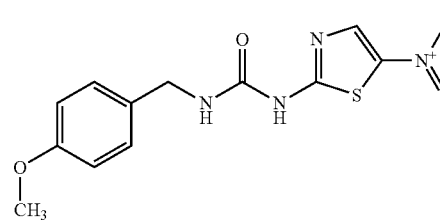 |
| GSK-3β Inhibitor XI | 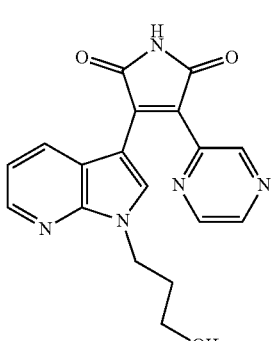 |
TABLE 4
| LSD1 Inhibitors | |
|---|---|
| Small Molecule | Chemical Structure |
| Tranylcypromine | 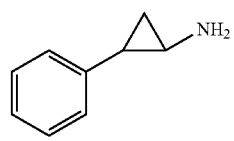 |
| Pargyline | 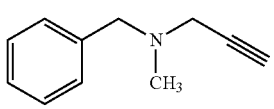 |
| Phenelzine | 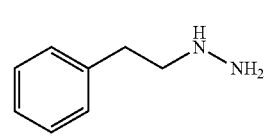 |

TABLE 4-continued

LSD1 Inhibitors

| Small Molecule | Chemical Structure |
|---|---|
| GSK2879552 | 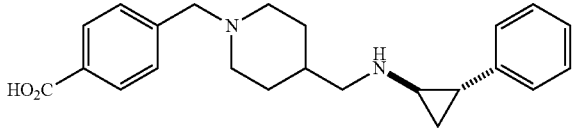 2 x HCl |

OAC compounds have the following structure with each substituent group listed in Table 5:

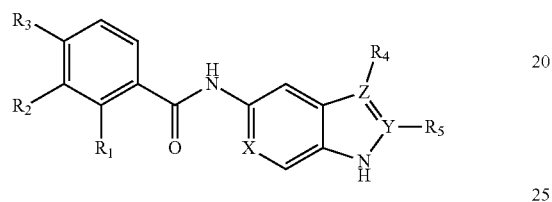

TABLE 5

OAC Compounds

| Compound | X | Y | Z | R1 | R2 | R3 | R4 | R5 | Oct4-luc Activity | Oct4-luc fold Induction | Enhance reprogramming efficiency |
|---|---|---|---|---|---|---|---|---|---|---|---|
| C1 | N | C | C | H | H | H | H | H | Active | 4.72 | YES |
| C2 | CH | C | C | H | H | H | H | H | Active | 4.15 | YES |
| C3 | CH | C | C | H | H | F | H | H | Active | 3.84 | YES |
| C4 | CH | C | C | H | H | MeO | H | H | Active | 5.46 | ND |
| C5 | CH | C | C | H | =N—O—N= | | H | H | Active | 2.87 | ND |
| C6 | CH | N | C | H | H | MeO | H | — | Active | 3.18 | ND |
| C7 | CH | N | C | H | H | F | H | — | Active | 2.2 | ND |
| C8 | CH | N | C | H | H | H | H | — | Active | 1.89 | ND |
| C9 | CH | N | C | H | H | EtO | H | — | Active | 7.22 | ND |
| C10 | CH | N | C | H | H | Et | H | — | Active | 4.51 | ND |
| C11 | CH | N | C | H | H | iso-Pr | H | — | Active | 3.78 | ND |
| C12 | CH | N | C | Cl | H | Cl | H | — | Active | 3.6 | ND |
| C13 | CH | N | C | H | Me | Me | H | — | Active | 2.78 | ND |
| C14 | CH | N | C | H | EtO | H | H | — | Active | 2.67 | ND |
| C15 | CH | N | C | H | MeO | H | H | — | Active | 1.93 | ND |
| C16 | CH | C | C | H | H | F | 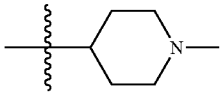 | H | Inactive | 1 | ND |
| C17 | CH | C | C | H | H | Me | CN | H | Inactive | 1.1 | ND |
| C18 | CH | N | C | H | F | H | H | — | Inactive | 1.27 | ND |
| C19 | CH | N | C | H | Cl | H | H | — | Inactive | 1.65 | ND |
| C20 | CH | N | C | H | Br | H | H | — | Inactive | 1.48 | ND |
| C21 | CH | N | C | H | CF3 | H | H | — | Inactive | 1.48 | ND |
| C22 | CH | N | C | F | H | H | H | — | Inactive | 1.5 | ND |
| C23 | CH | N | C | Cl | H | H | H | — | Inactive | 1.72 | ND |
| C24 | CH | N | C | Br | H | H | H | — | Inactive | 1.46 | ND |
| C25 | CH | N | C | MeO | H | H | H | — | Inactive | 1.5 | ND |
| C26 | CH | N | C | EtO | H | H | H | — | Inactive | 1.22 | ND |
| C27 | CH | N | C | MeO | MeO | H | H | — | Inactive | 1.37 | ND |
| C28 | CH | N | C | MeO | H | MeO | H | — | Inactive | 1.42 | ND |
| C29 | CH | N | C | H | MeO | MeO | H | — | Inactive | 1.13 | ND |
| C30 | CH | N | C | H | EtO | EtO | H | — | Inactive | 1 | ND |
| C31 | CH | N | N | H | Cl | H | — | — | Inactive | 1 | ND |
| C32 | CH | C | N | H | H | NO2 | — | Me | Inactive | 1.3 | ND |

Table 5 shows the Oct4-activating activity of compound C1 and its structural analogs. Compounds that induce Oct4-luc 1.8-fold or more were classified as being "active", and molecules that induce Oct4-luc less than 1.8-fold were indicated as being "inactive". ND: not determined.

These inhibitors and compounds are known in the art. Therefore, it is within the purview of one skilled in the art to select a suitable compound from each category and/or to select a suitable combination of different categories. For example, a TGF-β inhibitor is used in combination with a histone deacetylase inhibitor, or in combination with a histone deacetylase inhibitor and a GSK3β inhibitor. Other examples include the combination of a TGF-β inhibitor with a histone deacetylase inhibitor and a GSK3β inhibitor, a TGF-β inhibitor with a histone deacetylase inhibitor and an Oct4-activating compound, or a TGF-β inhibitor with a LSD1 inhibitor and an Oct4-activating compound. The combinations of a TGF-β inhibitor with different categories of at least one of a histone deacetylase inhibitor, a GSK3β inhibitor, a lysine specific histone demethylase 1 (LSD1) inhibitor, and an Oct4-activating compound are for illustration purposes only and are not intended to limit the scope of this invention.

In some embodiments, one or more small molecules include a combination of a histone deacetylase inhibitor VPA (V), a GSK3β inhibitor CHIR99021 (C), a TGF-β inhibitor 616452 (6), A-83-01 (A) or SB-431542 (S), a lysine specific histone demethylase LSD1 inhibitor tranylcypromine (T), and an Oct4-activating compound OAC1 (O). In some embodiments, the combination of the small molecules is "VC6TO," "VCATO," or "VCSTO," which includes the compounds disclosed herein. In a preferred embodiment, the combination comprises at least one small molecule that is a TGF-β inhibitor.

In some embodiments, the concentration of a TGF-β inhibitor, either used alone or in combination with one or more other small molecules, is within a range between 1 μM and 100 μM, between 2 μM and 50 μM, between 3 μM and 30 μM, between 5 μM and 10 μM. In some embodiment, the concentration of a TGF-β inhibitor is about 1 μM, about 2 μM, about 3 μM, about 4 μM, about 5 μM, about 6 μM, about 7 μM, about 8 μM, about 9 μM, about 10 μM, about 11 μM, about 12 μM, about 13 μM, about 14 μM, about 15 μM, about 20 μM, about 25 μM, about 30 μM, about 35 μM, about 40 μM, about 45 μM, or about 50 μM, without causing significant cytotoxicity.

Upon culturing the somatic tissue or cells in the presence of one or more small molecules for a period of between 7 days and 90 days, between 10 days and 60 days, between 15 days and 45 days or between 20 days and 30 days, the somatic tissue or cells are reprogrammed or converted into functional astrocytes or astroglial progenitor cells. It is within the purview of one skilled in the art to adjust the culturing period to optimize the percentage of conversion, for example, by choosing different combinations of the small molecules. The induced astrocytes or astroglial progenitor cells contain either or both of anterior and posterior subtypes. The induced astrocytes or astroglial progenitor cells can also contain either or both of dorsal and ventral subtypes.

As discussed in the examples below, the one or more small molecules disclosed herein can reprogram or convert somatic tissue or cells to astrocytes or astroglial progenitor cells. The mouse or human induced astrocytes resemble primary astrocytes in astrocytic gene expression and epigenetic status, and exhibit functional properties in promoting neuronal maturation, glutamate uptake and calcium signaling. Moreover, these cells can recapitulate Alexander disease phenotype of protein aggregation when expressing Gfap with a disease-causing mutation. The same compounds can also reprogram human fibroblasts into astroglial progenitor cells that can be further matured into functional astrocytes. Therefore, these induced astrocytes can be used in methods for preventing or treating neurodevelopmental disorders or neurological diseases that are associated with dysfunction of astrocytes. These induced astrocytes can also be used to screen and test candidate drugs for these diseases.

In some embodiments, this disclosure relates to a method of preventing or treating a neurodegenerative disease or a neurological disorder associated with astrocyte dysfunction in a subject. The method entails reprogramming or converting somatic tissue or cells into astrocytes or astroglial progenitor cells using one or more small molecule compounds as disclosed herein, and transplanting the astrocytes or astroglial progenitor cells into the brain of the subject suffering from the neurodegenerative disease or neurological disorder. In some embodiments, the somatic tissue or cells are autologous tissue or cells isolated from the subject to be treated. In some embodiments, the somatic tissue or cells that can be converted to astrocytes or astroglial progenitor cells include fibroblasts, urinary cells, and blood cells. The neurodegenerative diseases or neurological disorders associated with astrocyte dysfunction include, for example, Alzheimer's disease, Alexander disease, Parkinson's disease, Huntington disease, amyotrophic lateral sclerosis (ALS), multiple sclerosis (MS), epilepsy, stroke and cerebral ischemia.

The terms "treat," "treating," or "treatment" as used herein with regards to a condition refers to preventing the condition, slowing the onset or rate of development of the condition, reducing the risk of developing the condition, preventing or delaying the development of symptoms associated with the condition, reducing or ending symptoms associated with the condition, generating a complete or partial regression of the condition, or some combination thereof. In some embodiments, treating a condition means that the condition is cured without recurrence.

The working examples below further illustrate various embodiments of this disclosure. By no means the working examples limit the scope of this invention.

Example 1 Materials and Methods

Cell culture. MEFs and TTFs were derived from E13.5 embryos of Oct4-GFP transgenic (OG2) mice (Szabo et al., 2002), wild type or GFAP-GFP transgenic mice (Jackson Laboratory) (Zhuo et al., 1997). These cells were cultured in MEF medium containing DMEM, 10% FBS, 0.1 mM non-essential amino acids, and 2 mM L-glutamine. Mouse primary astrocytes were isolated from P1-2 pups following published protocol (Schildge et al., 2013) and cultured in DMEM containing 10% FBS.

Direct reprogramming mouse fibroblasts into astrocytes. MEFs were plated on 6-well or 12-well plates at a cell density of $3 \times 10^3$ cells/cm$^2$. Cells were cultured in MEF medium for 24 hr, then changed to mouse induced astrocyte medium (iAM) containing knock-out DMEM with 10% knock-out serum replacer, 10% FBS, 2 mM L-glutamine, 0.1 mM NEAA, 0.1 mM β-mercaptoethanol, and 100 ng/ml FGF. Cells were treated with compounds, including 500 nM valproaic acid (VPA) (Stemgent), 3 μM CHIR99021(D&C chemicals), 10 μM SB-431542 (D&C chemicals), 10 μM Tranylcypromine (Stemgent), and 1 μM OAC1(Li et al., 2012) for 10 days, replated onto Matrigel-coated plates (BD Biosciences) and continued with compound treatment for another 15 days. Cells were then switched to mouse astrocyte medium (AM) containing DMEM with 10% heat-inactivated FBS.

Immunocytochemistry. Cells were fixed in 4% paraformaldehyde (PFA) for 10 min, followed by washes in PBS at room temperature (RT). Cells were then blocked with 3% donkey serum in PBS containing 0.01% Triton-X 100 for 1 h at RT, and incubated with primary antibodies overnight at 4° C., then washed with PBS and incubated with secondary antibodies for 1 h at RT. Primary antibodies for GFAP (1:2000, DAKO, Z0334), S100μ (1:200, NOVUS, NB110-57478), ALDH1L1 (1:200, NeuroMab, 75-140), Synapsin (1:1000, SYSY, 106103), αB-crystallin (1:200, Enzo, ADI-SPA-223), MAP2 (1:500, GeneTex, GTX11268), Tuj1 (1:6,000, Covance, PRB-435P), NeuN (1:400, Millipore, MAB377), Pax6 (1:500, Covance, PRB-278P), Sox1 (1:500, Millipore, AB15766), Oligo2 (1:200, GeneTex, GTX62440), NG2 (1:500, Millipore, MAB5384), NKX2.2 (1:50, DSHB, 745A5) were used. Nuclei were stained with DAPI (1:6,000, Sigma, D9564).

Cell sorting and microarray gene expression analysis. GFAP-GFP positive iAs were sorted using the FACSAria III cell sorter (BD Bioscience). Gene expression profiling was performed using Mouse Gene 2.0 ST array (Affymetrix). Microarray data analysis was performed using Partek® Genomics Suite™ (Partek, Inc.). Expression values were Robust Multi-array Average (RMA) normalized (Irizarry et al., 2003). Fold-change values represent the linear ratio between signal intensities when the ratio value is greater than 1 and −1/ratio when the ratio is less than 1. Genes were defined as differentially expressed if they showed a fold-change value >1.5. Heatmaps to visualize differentially expressed genes were produced in Partek using Euclidian distance for hierarchical clustering of standardized expression values. Gene Ontology enrichment was performed for functional enrichment of commonly affected genes, with p-values calculated via Fisher's exact test. Microarray data have been deposited to NCBI's GEO under accession number GSE81927.

Real time PCR. Total RNA was extracted using Trizol reagent (Qiagen), cDNAs were prepared using Tetro cDNA synthesis kit (Bioline). Real time PCR was performed using DyNAmo Flash SYBR Green qPCR mix on a StepOnePlus system (Applied Biosciences) and normalized to β-Actin. Primers used are listed in Table 6 below.

| Gene | Forward sequence | Reverse sequence |
| --- | --- | --- |
| Gfap | GAAGTTCGAGAACTCCGGGAG | TTAGACCGATACCACTCCTCTG |
| mS100B | CCCTCATTGATGTCTTCCACCA | CTTCGTCCAGCGTCTCCATCAC |
| Aldh1L1 | GGAAGACAGCAGCCTGCCTG | CTTCACATTACTCAGGGCAC |
| NFIA | ACAGGTGGGGTTCCTCAATC | GAGGCTTGGTGTCTGGCATG |
| Ctnnal1 | GGAGAAGGTCACGGAGATCG | TGAAGTCCTCCACATCCTCC |
| Ndp | TGGACTCTCAACGCTGCATG | GGACAGTGCTGAAGGACACC |
| Lix1 | GGAGTTCATCATGGAGAGTG | CATTCCAGTGCAGTAGTTGG |
| Sox6 | CTTGCCGATGTGGTGGATAC | CTCTGCAAGGCTCTCAGGTG |
| TlrS | TCACTTGCTCATTCTCCCTT | GACCTCTCCATTCCTGGC |
| Let7b | TCGACTCGAGCCCTCTCACTGAACCTCTGTCTCC | GCGAATTCTTAATTAAAAACCACCCAATCTGTGGCTCCA |
| Col12a1 | AGGAGTTGATGAGCAGCTTG | GGTCACGAACATTGAGCGTG |
| Col6a3 | TCTTGAACGTGTGGCTAACC | TCTCCAGAGCACTTGCATGG |
| Col3a1 | GCCCACAGCCTTCTACAC | CCAGGGTCACCATTTCTC |
| Col1a1 | GCAACAGTCGCTTCACCTACA | CAATGTCCAAGGGAGCCACAT |
| P21 | AATCCTGGTGATGTCCGACC | CAAAGTTCCACCGTTCTCGG |
| ATF4 | GAGCTTCCTGAACAGCGAAGTG | TGGCCACCTCCAGATAGTCATC |
| P27 | GCCTGACTCGTCAGACAATC | CGTCTGCTCCACAGTGCCAG |
| DCN | TGAGCTTCAACAGCATCACC | AAGTCATTTTGCCCAACTGC |
| Gadd45b | CCTGGCCATAGACGAAGAAG | AGCCTCTGCATGCCTGATAC |
| IFRD1 | ACAGGCAGCTCTTGAAGGTC | AGACAGCGCTCAATGCTATC |
| TGFB1I1 | GCCTCTGTGGCTCCTGCAATAAAC | CTTCTCGAAGAAGCTGCTGCCTC |
| TGFBI | CCAAGTCACCCTACCAGCTG | TCCTCTGGTACCACTGCTTG |
| TSC22D1 | GCTGCTGCTGCTGTCTGAAC | ACATCCCTGCTCACTCTCTG |
| FOXG1 | TGGCAACACTGCCCATTCA | GCATTTGCGCAACACAGGTTA |

-continued

| Gene | Forward sequence | Reverse sequence |
|---|---|---|
| Hoxb4 | TTCACGTGAGCACGGTAAAC | CACTTCATGCGCCGATTCTG |
| NKX2.1 | AAAACTGCGGGGATCTGAG | TGCTTTGGACTCATCGACAT |
| Pax3 | ACTACCCAGACATTTACACCAGG | AATGAGATGGTTGAAAGCCATCAG |
| Sox1 | CCAAGAGACTGCGCGCGCTG | TGAGCAGCGTCTTGGTCTTG |
| Pax6 | ACCAAAGGGTCATCGCGCCC | TGGCAGTCCTTGCGATCGGC |
| Oct4 | TAGGTGAGCCGTCTTTCCAC | GCTTAGCCAGGTTCGAGGAT |
| Nanog | CAGGAGTTTGAGGGTAGCTC | CGGTTCATCATGGTACAGTC |
| AOP4 | TTCTCTTCGGTGCTAGGAAAC | AGGAAGCTTATGTCTCTGGTG |
| Glast1 | CTAGTTGTCTTCTCCATGTG | AGGAGAGGCAGGACGATGAC |
| Glt1 | GCGCATGTGCGACAAGCTGG | GCGATGCCAAGCGAAGCAGC |
| 36B4 | TGGTGCTGATGGGCAAGAA | ATTCCCCCGGATATGAGGC |
| Actin | CCGGCGTGGCTACAGCTTC | ACCTGGCCGTCAGGCAGCTC |
| mGfap | TTGTTGGTATGGAGTATAGGTTGTTGTTAT | CCTACCTTCCTCTACCCATACTTAAACT |

Astrocyte-neuron co-cultures. Mouse cortical neurons were isolated from E13.5 mouse embryo and cultured in neuronal culture media (neurobasal, 1× B27, 2 mM L-glutamine) alone or directly on a layer of induced astrocytes (iA), mouse primary astrocytes (pA) or MEF for 5 days. Mouse neurons, iA, pA or MEFs were plated at the same density of 10,000 cells/cm$^2$. The co-cultured cells were stained for MAP2 and Synapsin. The Synapsin+puncta along the MAP2+ neurites were expressed as the number of puncta per 50 μm neurite length.

Transplantation. Induced astrocytes labeled by GFP-expressing lentivirus were dissociated using trypsin-EDTA and resuspended in medium at 100,000 cells/μl density and kept on ice. Two μl cell suspensions were injected 1 mm from the midline between the Bregma and Lambda and 1 mm deep into the anterior lateral ventricles of immunodeficient neonatal NSG mice. After 6 weeks, mice were euthanized and perfused with 4% PFA for 5 min. Brain tissues were harvested for immunostaining. All animal work was performed under the IACUC protocol approved by the City of Hope IACUC Committee.

Ca$^{2+}$ imaging. Cells were seeded in 12-well plates at a density of 1×10$^5$ cells per well and stimulated with 10 μM glutamic acid. Fluo-4 Calcium Imaging Kit (Invitrogen F10489) was used to monitor calcium waves following manufacturer's instructions. Calcium waves were captured using a Zeiss Observer Microscope. Wave intensity was analyzed using Image Pro Premier and the intensity was measured as ΔF/F0=(F−F0)/F0.

Bisulfite sequencing. Genomic DNAs were isolated from MEF, FACS-sorted induced astrocytes and mouse primary astrocytes using a Genomic DNA Purification Kit (Qiagen). Bisulfite conversion of genomic DNAs was carried out using the EZ DNA Methylation-Gold Kit (Zymo Research). The bisulfite-modified DNA was then used as a template for PCR to amplify the promoter region of Gfap. The amplified products were cloned into the pCR2.1-TOPO cloning vector (Invitrogen), and 10 randomly selected clones were sequenced using T7 or M13R primers.

Glutamate uptake assay. The glutamate uptake was measured using the Glutamate Assay Kit (BioVision). Induced astrocytes were plated at a concentration of 2×10$^4$ cells per well in a 24-well plate. 100 μM L-glutamate was added to each well. After incubation for 6 h, the glutamate concentration in the media was measured and presented as nmol of glutamate per mg of total proteins.

Transfection into induced astrocytes. Induced astrocytes (iA) were seeded at 1×10$^5$ cells per well in 12-well plates and incubated overnight. Then 2 μg plasmid of human wild type (WT) GFAP-GFP or AxD mutant GFAP-GFP with the R239C mutation (Bachetti et al., 2008) was transfected into iA using Lipofectamine® 2000 (Invitrogen). Forty eight hr after transfection, cells were assayed by immunostaining. For drug treatment, 24 hr after transfection, cells were treated with vehicle control or 100 μM ceftriaxone for 48 hr, followed by immunostaining.

Inducing human fibroblasts for astrocytic conversion. Human fibroblasts were purchased from Millipore (SCC058) or Coriell (AG14048) and tested for lack of mycoplasm contamination. Human fibroblasts were seeded onto 6-well plates at the density of 10$^4$ cells/cm$^2$ and cultured in either FibroGRO complete medium (for SCC058) or Eagle's MEM with 15% non-inactivated fetal bovine serum (for AG14048) for 24 hr, then switched to induced astrocyte medium containing DMEM/F12 with 2 mM L-glutamine, 0.1 mM NEAA, 1×N2, 1×B27 and 100 ng/ml FGF. For SCC058, cells were treated with VCSTO compounds, including 500 nM VPA (Stemgent), 3 μM CHIR99021 (D&C chemicals), 10 μM SB-431542 (D&C chemicals), 10 μM Tranylcypromine (Stemgent), and 1 μM OAC1 (Li et al., 2012) for 20 days, replated onto Matrigel-coated plates and continued with compound treatment for another 20 days. Cells were then treated with 10 ng/ml CNTF for another 6 days. For AG14048, cells were treated with VCSTO compounds at the same concentration as described above for 30 days, then treated with VCSTO together with 10 ng/ml CNTF for another 10 days.

FSP1 FACS analysis. MEFs were stained by FSP1 antibody (Millipore, ABF32). FACS analysis was performed on Flow Cytometry Analyzers BD Fortessa (BD Bioscience).

Statistical analysis. Independent-samples t-test was used to compare means of two independent samples. A value of p<0.05 was considered statistically significant.

Example 2 A Compound Cocktail Induced the Conversion from MEFs to Astrocyte-Like Cells A compound combination including the histone deacetylase inhibitor VPA (V), the GSK3β inhibitor CHIR99021 (C), the TGFβ inhibitor 616452 (6), the lysine specific histone demethylase LSD1 inhibitor Tranylcypromine (T), the cyclic AMP inducer forskolin (F), and a histone methylation inhibitor DZNep (Z) was used to reprogram mouse embryonic fibroblasts (MEFs) into iPSCs (Hou et al., 2013). In this chemical cocktail, compounds F and Z were used together to induce the expression of Oct4, a factor critical for reprogramming. It was also reported that a small molecule OAC1 was used as an Oct4-activating compound (Li et al., 2012). In this example, the combination of VC6T with the OAC1 compound (together termed VC6TO) was tested to reprogram MEFs into iPSCs. MEFs were derived from mice harboring an Oct4 promoter-driven GFP (OG2) reporter. However, treatment with VC6TO for up to 25 days failed to induce any Oct4-GFP-positive iPSC colonies from the OG2 MEFs. Instead, cells with astrocyte-like morphology were observed (FIG. 1A).

Figure 2:
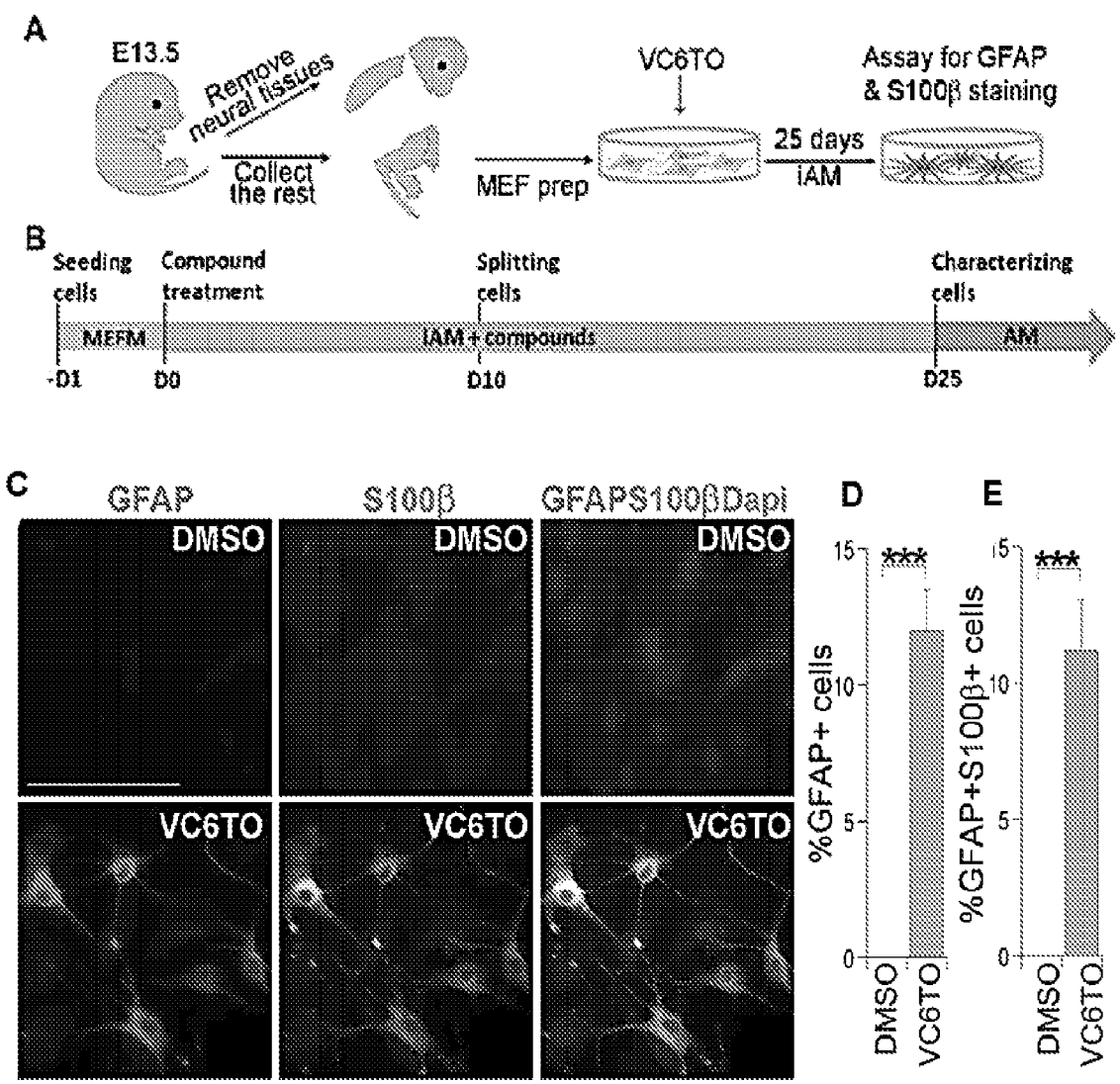
FIGS. 2A-2E also illustrate direct reprogramming MEF into astrocyte-like cells by VC6TO.

Subsequently, the VC6TO cocktail was tested to see if it could reprogram MEFs into astrocytes. Any neural tissues was excluded from the MEF preparation (FIG. 2A) as described (Vierbuchen et al., 2010). Immunostaining MEFs with various neural lineage markers revealed no contamination of neural progenitor cells, neurons, astrocyes, and oligodendrocyte progenitor cells (FIG. 1B), instead 99.6% cells expressed the fibroblast marker FSP1 (FIG. 1O). These MEFs were treated with VC6TO and cultured in induced astrocyte medium (FIG. 2B). Twenty-five days after compound treatment, the resultant cells were immunostained for astrocyte markers, glial fibrillary acidic protein (GFAP) and S100β. 12% GFAP-positive cells with typical astrocyte morphology were detected (FIG. 2C, 2D). The percentage of GFAP+S100β+ cells was similar to that of GFAP+ cells (FIG. 2E). Together, these results indicate that the VC6TO compounds can reprogram MEFs into GFAP-positive and S100β-positive astrocyte-like cells.

Example 3 A TGF Inhibitor was Critical for Astrocytic Conversion

Figure 3:
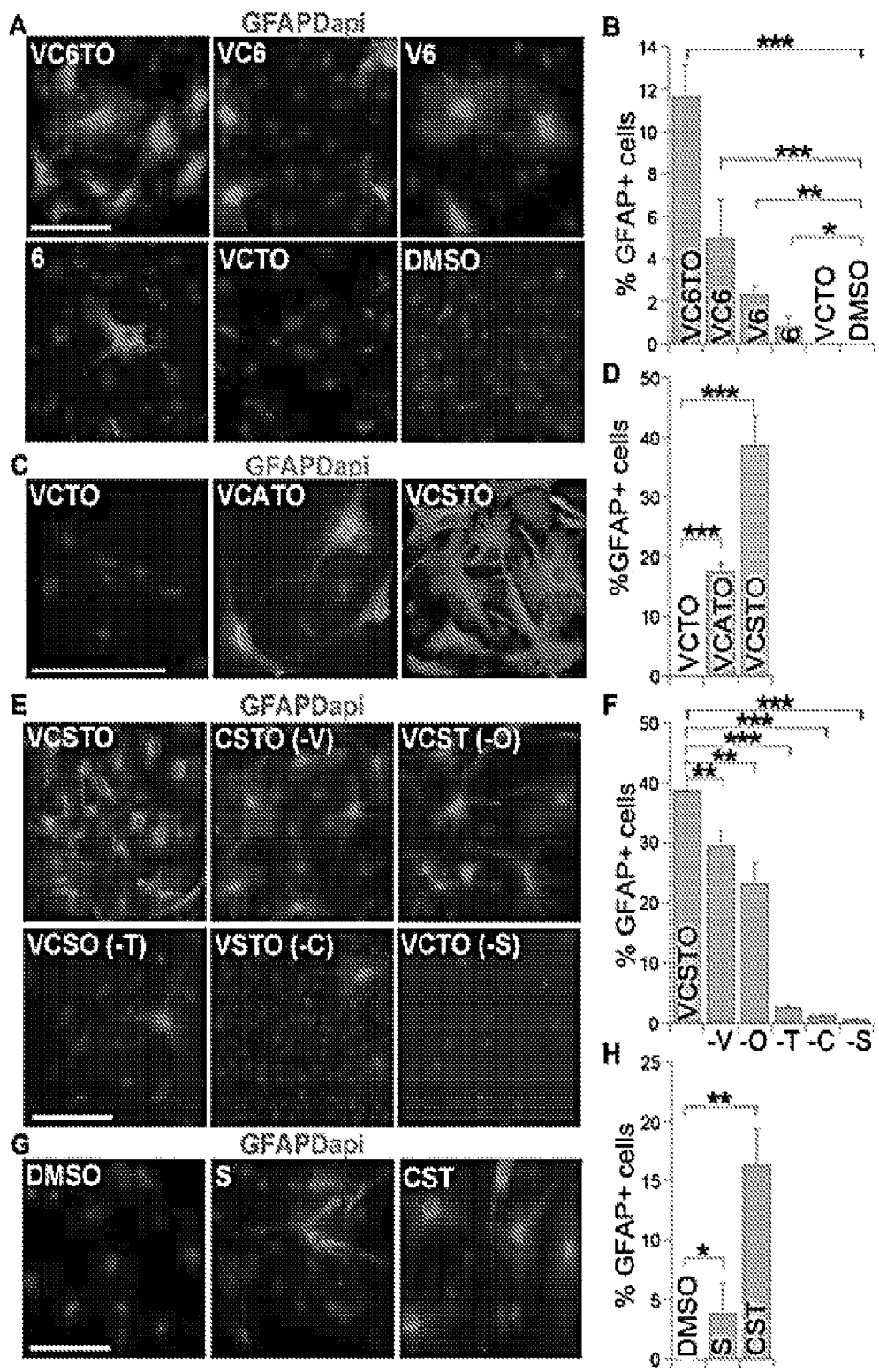
FIGS. 3A-3H illustrate that a TGFβ inhibitor is critical for astrocytic reprogramming.

Compounds critical for astrocytic conversion were identified. The combination of VC6, V6, or 6 alone, was able to induce GFAP-positive cells from MEFs, although the efficiency of conversion decreased when the number of compounds was reduced. In contrast, subtraction of compound 6 from VC6TO led to failure of astrocytic conversion, as revealed by the lack of GFAP-positive cells (FIG. 3A, 3B). These results suggest that compound 6 is necessary and sufficient to induce the conversion of MEFs into astrocyte-like cells.

Since compound 6 is a transforming growth factor β (TGFβ) receptor 1 kinase inhibitor (Gellibert et al., 2004), other inhibitors of TGFβ receptor 1 were tested for inducing astrocytic reprogramming together with VCTO. Compound A-83-01 (A) or SB-431542 (S), two well-characterized inhibitors of TGFβ receptor 1 (Inman et al., 2002; Tojo et al., 2005) was tested. Treating MEFs with either the combination of VCTO with A (VCATO) or VCTO with S (VCSTO) induced a substantial increase in GFAP-positive cells with astrocyte morphology (FIG. 3C, 3D). In contrast, VCTO did not induce any GFAP-positive cells (FIG. 3C, 3D). VCATO and VCSTO induced more GFAP-positive cells than the initial VC6TO combination (FIG. 3B-3D), with the highest conversion efficiency observed with VCSTO, which induced 38% GFAP-positive cells at day 25 after compound treatment. The rest of the study was focused on VCSTO-induced reprogramming.

Individual compounds were subtracted from VCSTO to determine the effect of individual compounds on astrocytic conversion. Similar to removal of 6, subtraction of S from VCSTO led to almost complete loss of GFAP-positive cells (FIG. 3E, 3F). Subtraction of T or C decreased reprogramming efficiency dramatically, whereas removal of V or O reduced the efficiency mildly (FIG. 3E, 3F). On the other hand, compound S by itself was sufficient to induce GFAP-positive cells from MEFs (FIG. 3G, 3H). Combination with C and T led to a more robust induction of GFAP-positive cells (FIG. 3G, 3H). These results indicate that compound S is critical for astrocytic reprogramming, while compounds C and T promote reprogramming efficiency.

Figure 4:
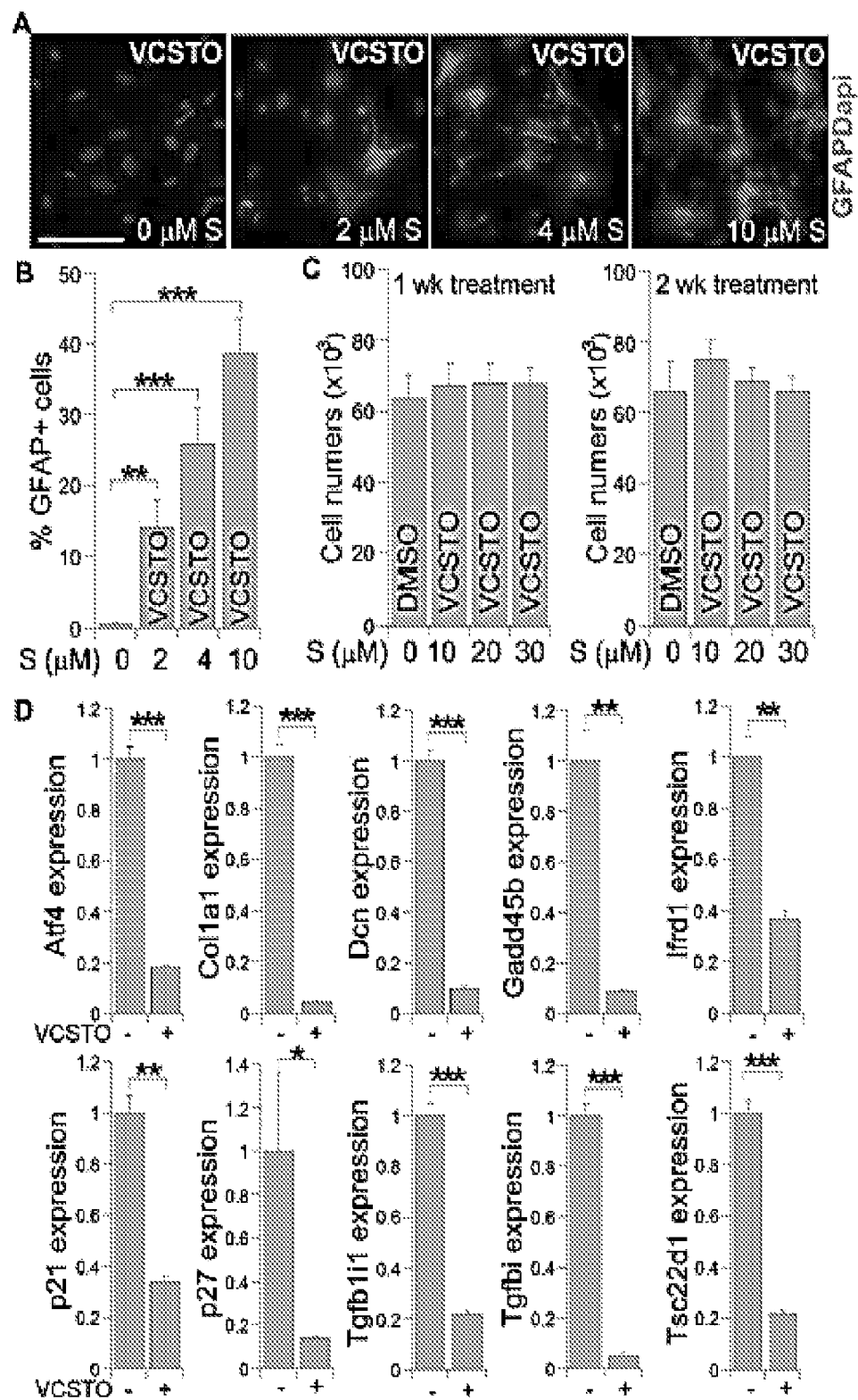
FIGS. 4A-4D illustrate that the treatment with VCSTO inhibited TGFβ target genes.

Since S was identified as a critical compound for astrocytic reprogramming, the dose response of compound S was determined. MEFs were treated with VCSTO at different concentrations of S from 0 to 10 μM, and observed increased GFAP-positive cells with elevated concentrations of S (FIG. 4A, 4B). No toxicity was observed in cells treated with VCSTO at the concentration of S at 10 μM or even higher (20 or 30 μM) (FIG. 4C).

Since S is an inhibitor of TGFβ receptor 1 (Inman et al., 2002), whether the TGFβ signaling is suppressed by VCSTO treatment was tested. After 24 hr VCSTO treatment of MEFs, dramatic inhibition of gene expression was observed for a set of TGFβ downstream effectors (FIG. 4D), including Atf4, Col1a1, decorin (Dcn), Gadd45b, Ifrd1, p21, p27, Tgfb1i1, Tgfbi, and Tsc22d1, consistent with the role of S in inhibiting TGFβ signaling. These results indicate that a TGFβ inhibitor is critical for converting fibroblasts into astrocyte-like cells.

Figure 5:
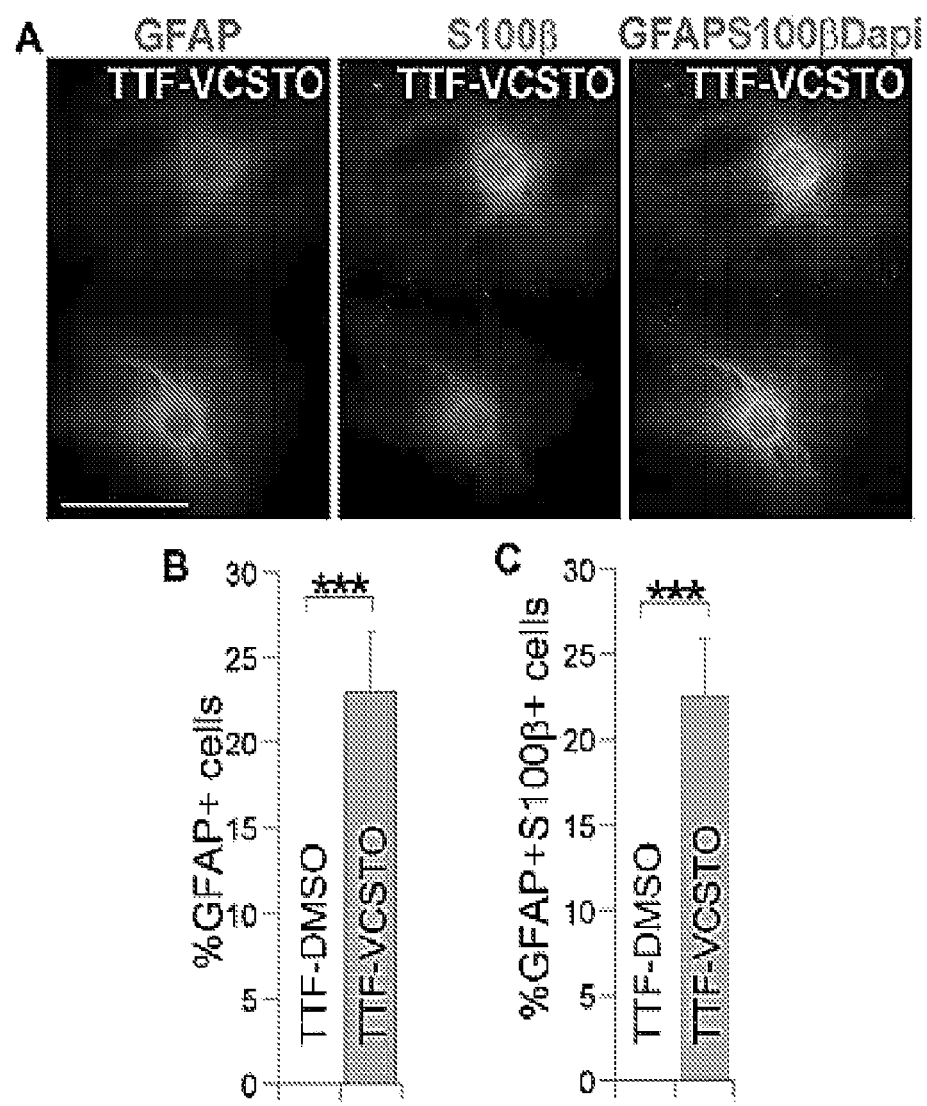
FIGS. 5A-5C illustrate astrocytic reprogramming by VCSTO in tail tip fibroblasts.

To determine if astrocyte-like cells could also be converted from other cell types, mouse tail-tip fibroblasts (TTFs) were treated with VCSTO compounds. Twenty-five days after VCSTO treatment, GFAP-positive and S100β-positive cells with astrocyte morphology were detected (FIG. 5A). The percentage of GFAP+S100β+ cells was similar to that of GFAP+ cells (FIG. 5A-5C).

Figures 6A, 6B, 6C, 6D:
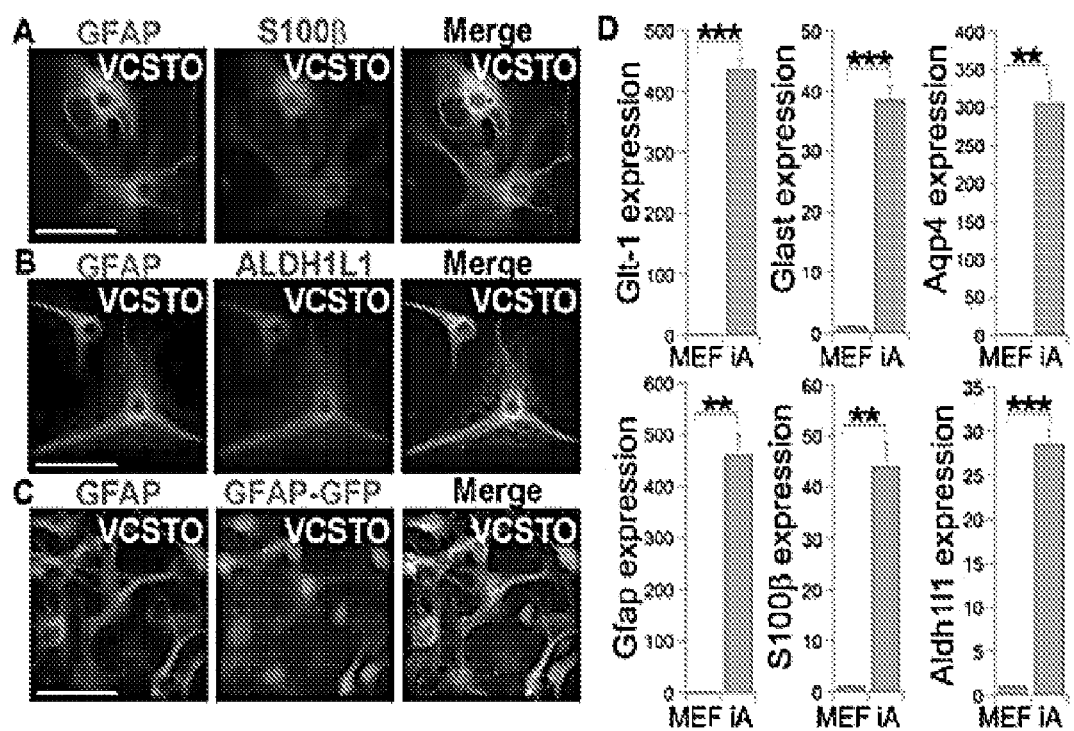
FIGS. 6A-6I illustrate expression of astrocytic markers from VCSTO-induced cells.

Example 4 VCSTO-Induced Cells Express Astrocytic Genes and Exhibit Epigenetic Reprogramming To verify that the VCSTO-reprogrammed cells were indeed astrocytes, astrocytic marker expression in these cells was first determined. Double staining for GFAP and S100β revealed that the VCSTO-induced cells expressed both GFAP and S100β (FIG. 6A). In addition to GFAP and S100β, ALDH1L1 has been identified to be a reliable marker for astrocytes (Barres, 2008). Double staining the VCSTO-reprogrammed cells with GFAP and ALDH1L1 revealed that the compound-induced cells were positive for both of these astrocytic markers (FIG. 6B). These results further confirmed the astrocyte identity of the VCSTO-induced cells.

Because astrocytes could be visualized by GFP fluorescence in the GFAP-GFP reporter mice (Zhuo et al., 1997), MEFs from these mice were derived and treated with VCSTO to monitor astrocytic conversion. GFAP-GFP-positive cells emerged around day 10 to day 15 after VCSTO treatment. The induced cells were visualized for GFAP-GFP fluorescence and immunostained for GFAP at day 25 after VCSTO treatment. Nearly all GFAP-GFP positive cells were also positive for GFAP immunostaining (FIG. 6C).

Astrocytes express high levels of glutamate transporters, predominantly GLT-1 and GLAST (Chaudhry et al., 1995). Aquaporin 4 (AQP4), a member of the aquaporin family of membrane proteins, is also enriched in astrocytes (Simard and Nedergaard, 2004). Real time PCR revealed that the VCSTO-reprogrammed cells expressed high levels of Glt-1, Glast, and Aqp4, in addition to the astrocytic markers Gfap, S100β, and Aldh1l1 (FIG. 6D), further strengthening the conclusion that the VCSTO-reprogrammed cells are astrocytes.

Figures 6E, 6F, 6G, 6H, 6I:
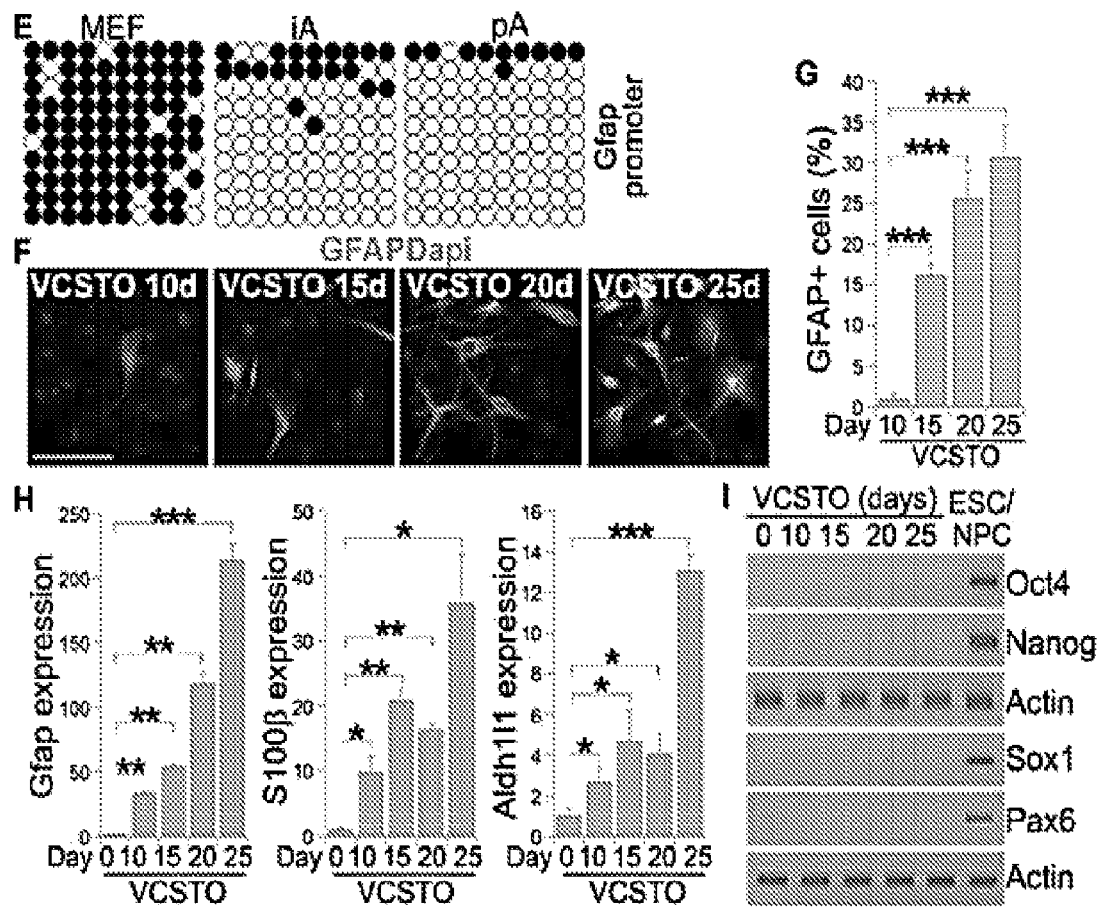

An important aspect of reprogramming is epigenetic reprogramming. Demethylation of the Gfap promoter has been shown to be associated with astrocyte differentiation (Hatada et al., 2008). The Gfap promoter was tested to see if it is demethylated during astrocytic conversion from MEFs. VCSTO-induced cells were sorted for GFAP-positive cells after GFAP staining. The resultant cells were subjected to DNA methylation analysis. Bisulfite sequencing revealed that the Gfap promoter of VCSTO-induced cells was largely demethylated, similar to that in primary astrocytes (FIG. 6E), whereas the Gfap promoter in parental MEFs was highly methylated (FIG. 6E). This result indicates that epigenetic reprogramming occurred during VCSTO-induced astrocytic conversion.

To determine the dynamic expression pattern of astrocytic genes during the conversion, MEFs were treated with VCSTO for various time periods and immunostaining and RT-PCR were performed at days 10, 15, 20 and 25. GFAP-positive cells were seen at day 10 after compound treatment, although the efficiency was low (FIG. 6F, 6G). By day 15, more than 15% GFAP-positive cells were detected. The rate of conversion further increased with time. By day 25, GFAP-positive cells reached more than 30% (FIG. 6F, 6G). In parallel RT-PCR analysis, increased expression of the astrocytic markers Gfap, S100β, and Aldh1l1 was observed along the time course, with the highest induction at day 25 (FIG. 6H). In contrast, the induction of the pluripotency genes Oct4 and Nanog, and the neural progenitor genes Sox1 and Pax6, was not observed during the same time course (FIG. 6I), suggesting that these compounds induce astrocytic conversion without inducing iPSC or neural progenitor cell intermediates.

Figures 7A, 7B:
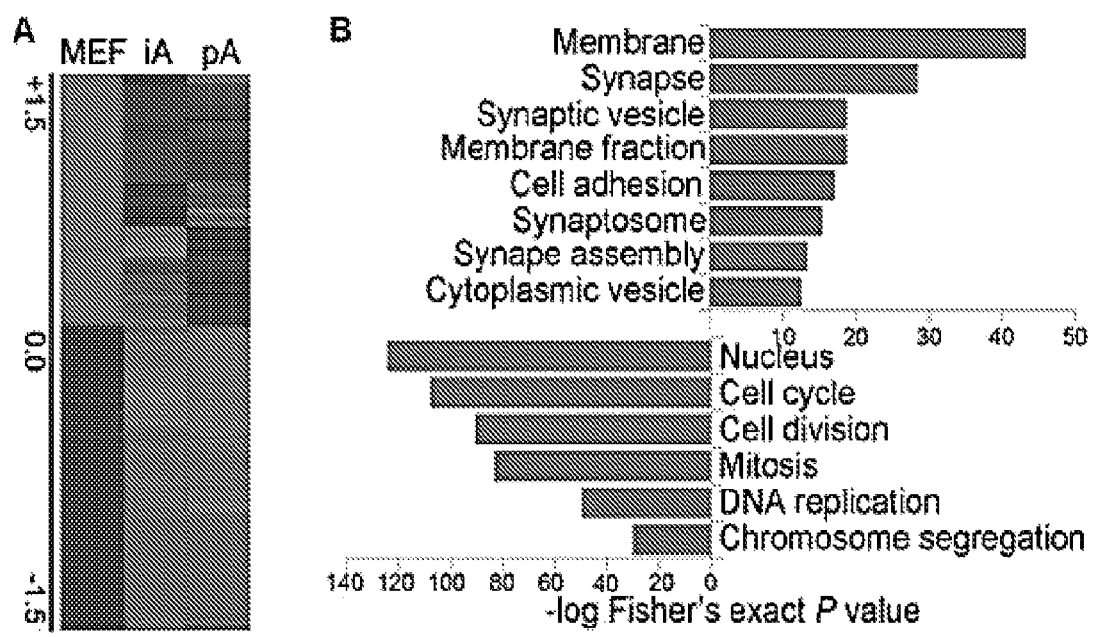
FIGS. 7A-7G illustrate genomic-wide transcriptional profiling of VCSTO-induced astrocytes.
Figure 8A:
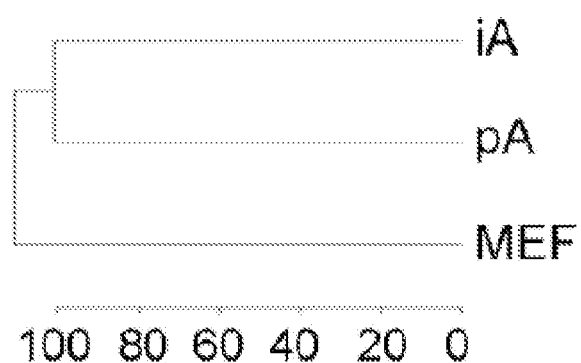
FIGS. 8A-8E illustrate gene expression analysis of VCSTO-induced astrocytes.
Figure 8B:
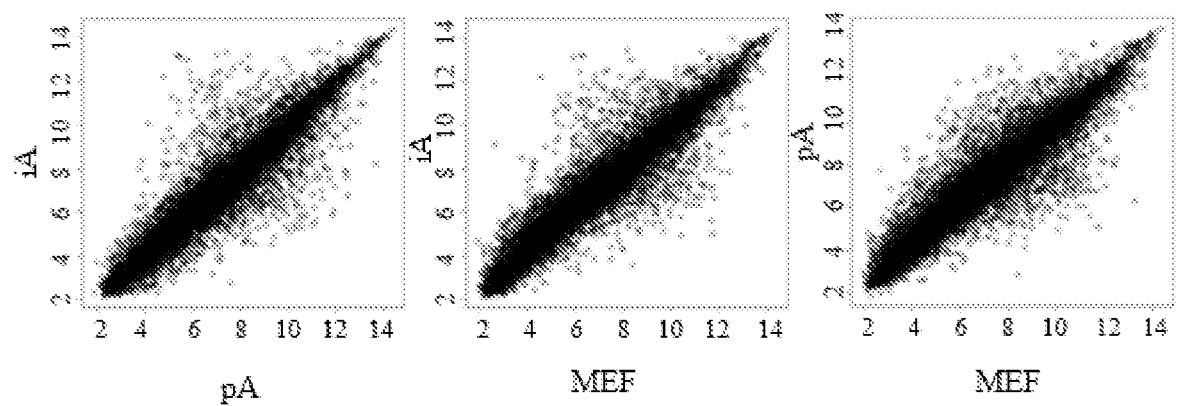

Example 5 Genome-Wide Remodeling and Regional Specification in VCSTO-Induced Astrocytes Genome-wide profiling was performed to compare gene expression pattern of VCSTO-induced astrocytes with that of primary astrocytes and MEFs. MEFs were derived from GFAP-GFP reporter mice and treated with VCSTO for 25 days. The reprogrammed cells were sorted for GFAP-GFP-positive cells and subjected to DNA microarray analysis, along with primary astrocytes and MEFs. A heatmap depicting all probe sets that were differentially expressed by at least 1.5-fold showed that the transcriptional program characteristic of MEFs was globally reprogrammed toward that of astrocytic lineage (FIG. 7A). Hierarchical clustering revealed that the overall gene expression pattern in induced astrocytes is more similar to that in primary astrocytes than to parent MEFs (FIG. 8A, 8B). Among the genes up-regulated (≥2-fold) in primary astrocytes compared to MEFs, 53.9% were also up-regulated in iA; among the genes down-regulated in primary astrocytes relative to MEFs, 68.3% were also down-regulated in iA. Genes up-regulated in both induced astrocytes and primary astrocytes, compared to MEFs, were significantly enriched for gene ontology (GO) terms associated with membrane and synapse (FIG. 7B), consistent with the critical role of astrocytes in synaptogenesis (Hama et al., 2004; Eroglu and Barres, 2010). In contrast, genes down-regulated in both induced astrocytes and primary astrocytes, compared to MEFs, were significantly enriched for GO terms linked to cell cycle and cell division (FIG. 7B).

Figures 7C, 7D, 7E, 7F, 7G:
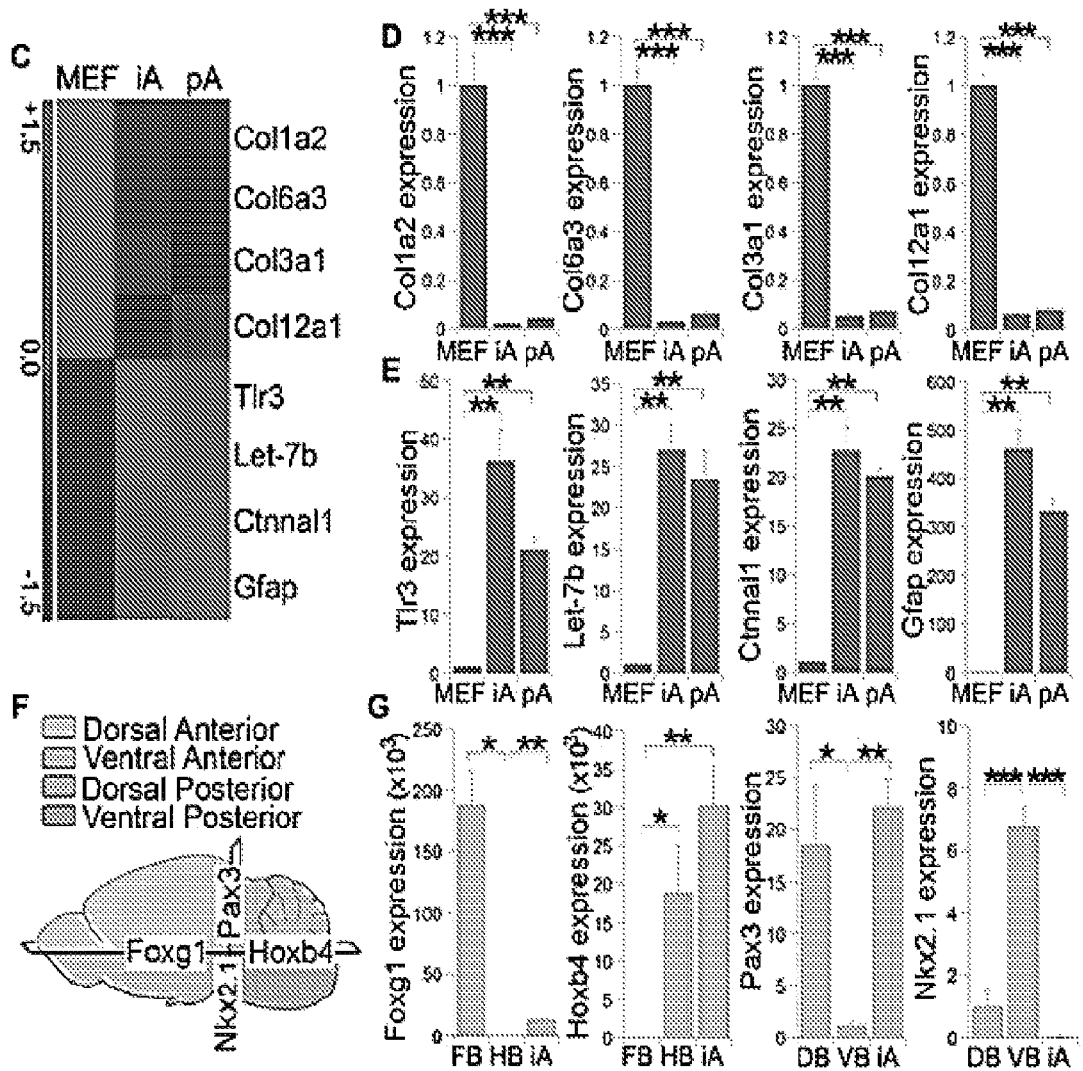
Figure 8C:
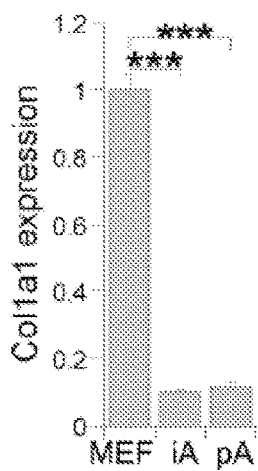
Figure 8C:
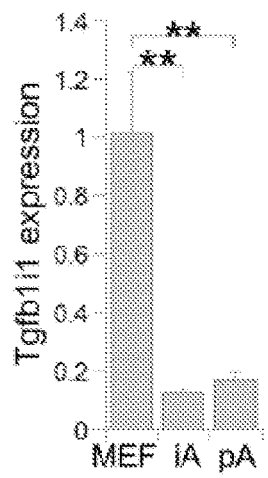
Figure 8C:
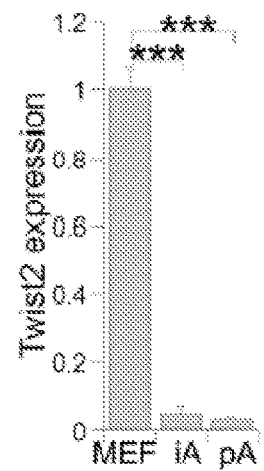
Figure 8D:
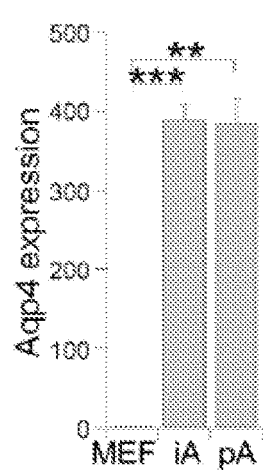
Figure 8D:
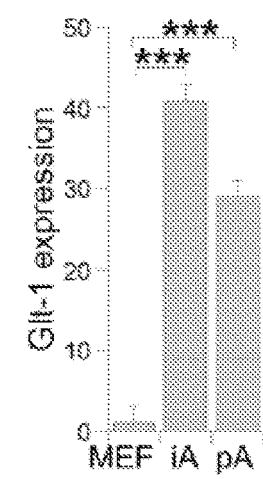
Figure 8D:
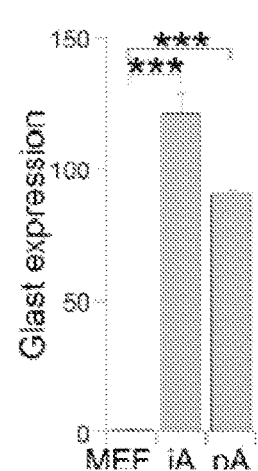

Validation of differentially expressed genes revealed that the known fibroblast-related genes were down-regulated in both VCSTO-induced astrocytes and primary astrocytes, compared to MEFs (FIG. 7C, 7D, FIG. 8C). In contrast, genes that are known to be expressed in astrocytes or involved in astrocyte differentiation and functions were strongly up-regulated in both induced and primary astrocytes, compared to MEFs (FIG. 7C, 7E, FIG. 8D). These results indicate that induced astrocytes resemble primary astrocytes in genome-wide gene expression profile.

Figure 8E:
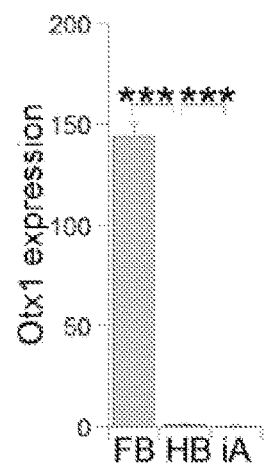
Figure 8E:
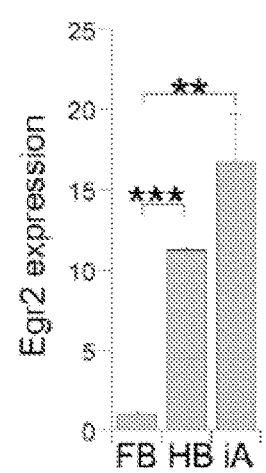
Figure 8E:
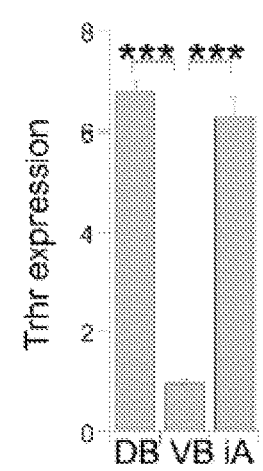
Figure 8E:
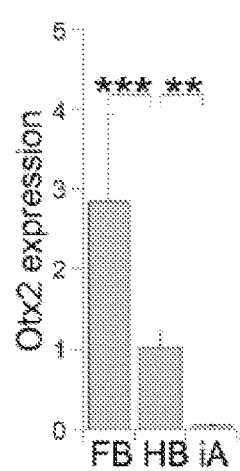
Figure 8E:
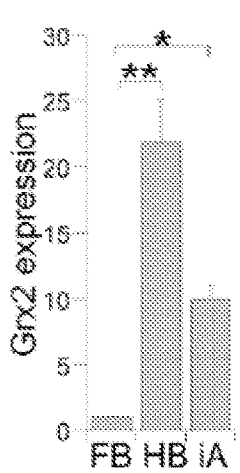
Figure 8E:
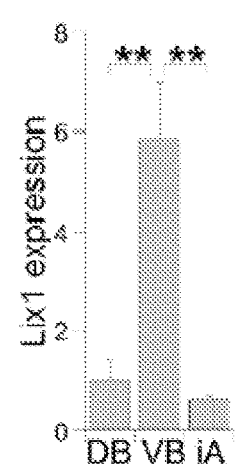

To determine the regional subtypes of VCSTO-induced astrocytes, real time PCR was performed to measure the expression levels of markers for forebrain (Foxg1, Otx1, Otx2), hindbrain (Hoxb4, Egr2, and Grx2), dorsal (Pax3, Trhr) and ventral (Nkx2.1, Lix1) brains (FIG. 7F & FIG. 8E). Induced astrocytes expressed both the forebrain markers Foxg1, Otx1 and Otx2, and the hindbrain markers Hoxb4, Egr2 and Grx2, although the expression of the hindbrain markers is more robust (FIG. 7G & FIG. 8E), suggesting that induced astrocytes contain both anterior and posterior astrocyte subtypes, perhaps with a more abundant subpopulation of posterior astrocytes. As for the dorsal-ventral regionality, VCSTO-induced astrocytes are predominantly dorsal, exhibiting robust Pax3 and Trhr expression, but barely detectable Nkx2.1 and Lix1 expression (FIG. 7G & FIG. 8E). These results indicate that the chemically induced astrocytes can be regionally specified.

Example 6 VCSTO-Induced Astrocytes are Functional

Figures 9A, 9B, 9C, 9D, 9E:
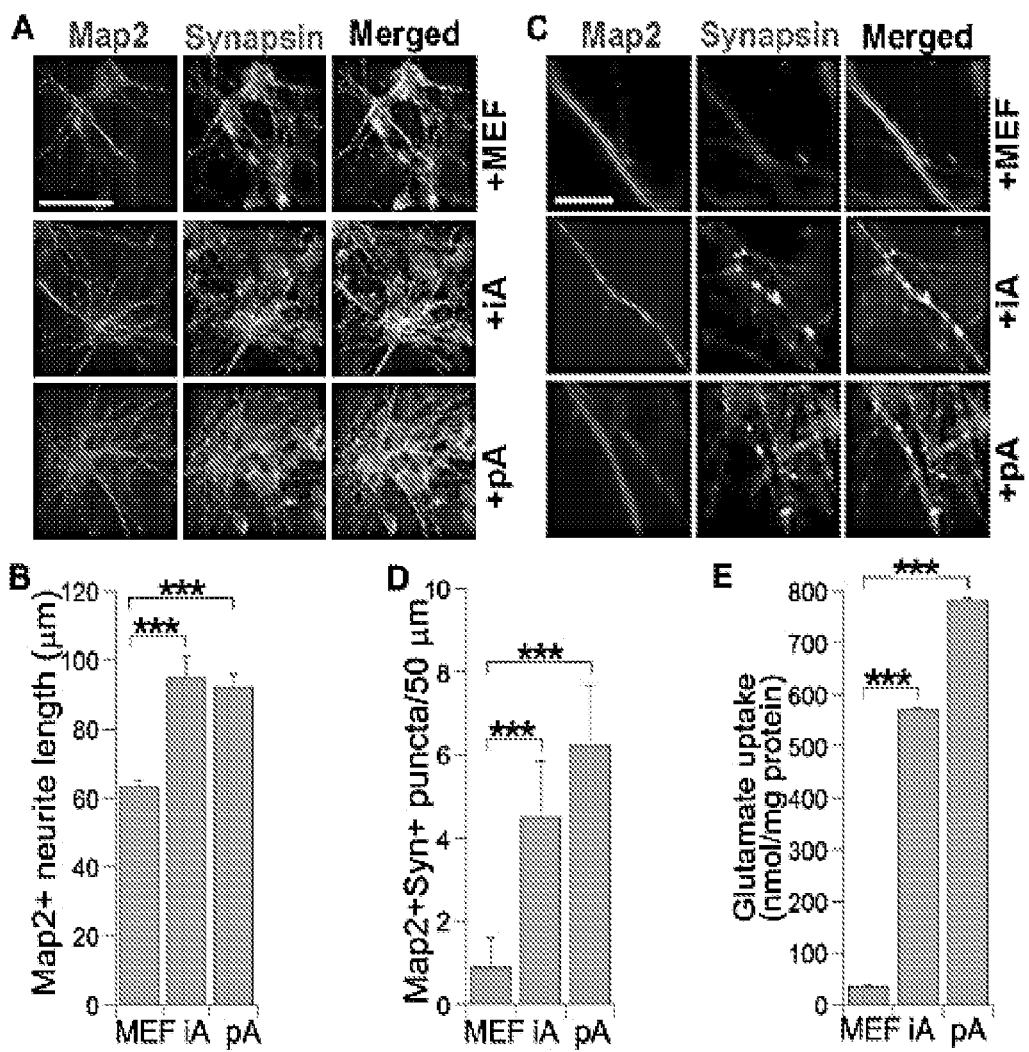
FIGS. 9A-9I show that compound-induced astrocytes are functional.
Figure 10:
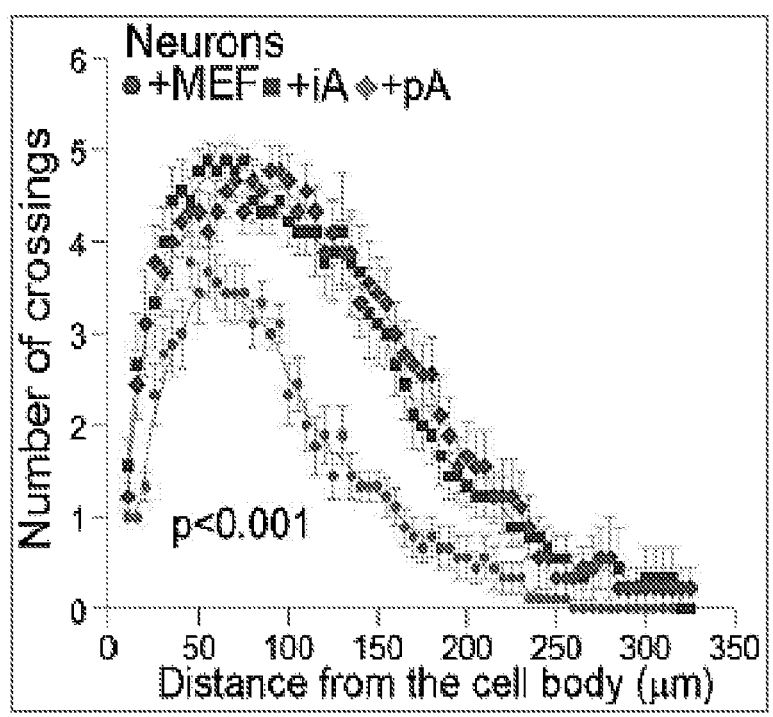
FIG. 10 illustrates Sholl analysis of neurite complexity in co-cultured neurons. Neurons were co-cultured with MEF, induced astrocytes (iA), or mouse primary astrocytes (pA), respectively. Errors bars are sd of the mean.

To test if compound-induced astrocytes possess astrocyte function to promote neuronal maturation and synaptic formation, the induced astrocytes were co-cultured with mouse primary cortical neurons. Neuronal maturation was evaluated by immunostaining with a mature neuronal marker, MAP2, at day 5 after co-culture. Both total neurite length and neurite complexity were increased in neurons co-cultured with induced astrocytes or primary astrocytes, compared to that in neurons co-cultured with MEFs (FIG. 9A, 9B & FIG. 10). Moreover, the density of synapsin-positive puncta along the MAP2-positive neurites was significantly increased in neurons co-cultured with induced astrocytes and primary astrocytes, compared to that in neurons co-cultured with MEFs (FIG. 9C, 9D). These results indicate that the VCSTO-induced astrocytes exhibit functional property in promoting neuronal maturation and synaptogenesis, like primary astrocytes.

Next, whether the compound-induced astrocytes were functional in glutamate uptake was determined. Primary astrocytes, induced astrocytes and parental MEFs were cultured in media containing glutamate for 6 hr, the concentration of glutamate in the media was measured to determine glutamate uptake. Both induced astrocytes and primary astrocytes exhibited substantial glutamate uptake, compared to MEFs (FIG. 9F), indicating that compound-induced astrocytes are functional in glutamate uptake.

Figures 9F, 9G, 9H, 9I:
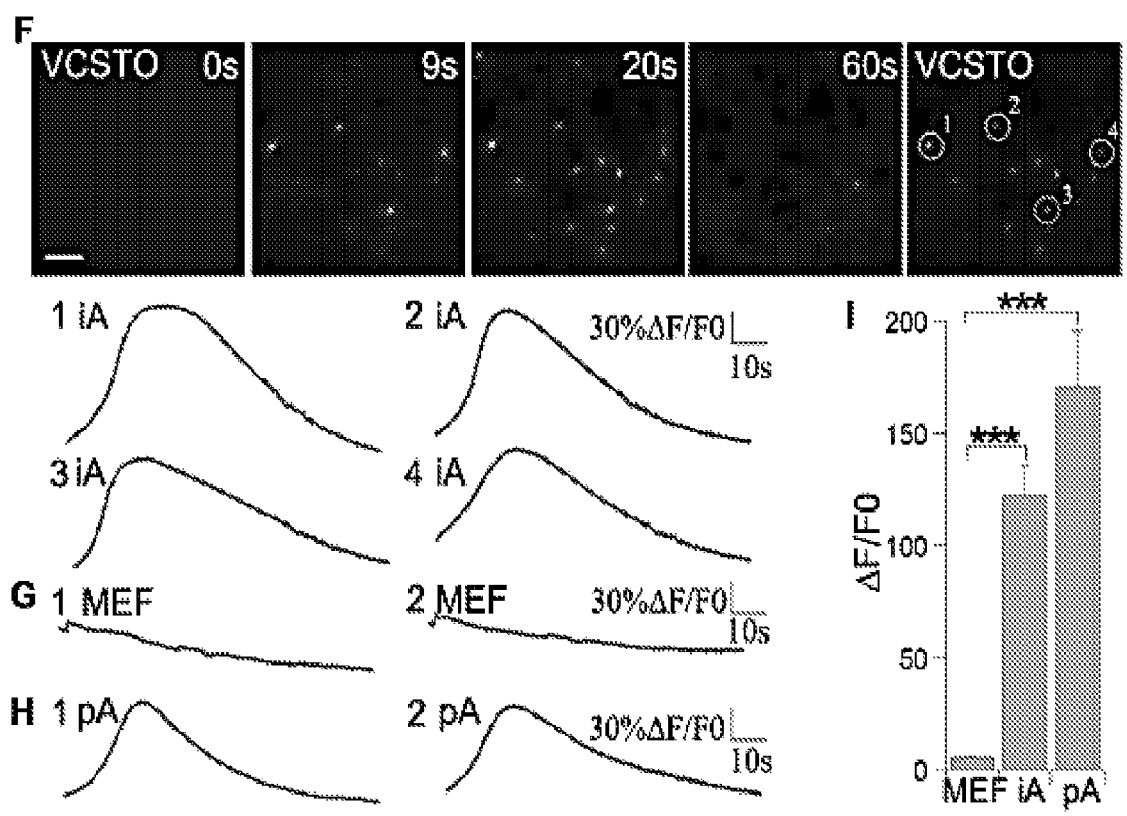

Calcium imaging analysis revealed that the VCSTO-induced astrocytes exhibited glutamate-induced calcium spikes, in a manner similar to primary astrocytes, whereas MEFs did not respond to glutamate stimulation with calcium spikes (FIG. 9G-I). These results suggest that induced astrocytes acquire the ability to respond to neurotransmitters through calcium signaling, like primary astrocytes. In summary, the chemically induced astrocytes are functional astrocytes with the ability to promote neuronal survival and maturation, uptake glutamate and respond to calcium signaling.

Figures 11A, 11B, 11C:
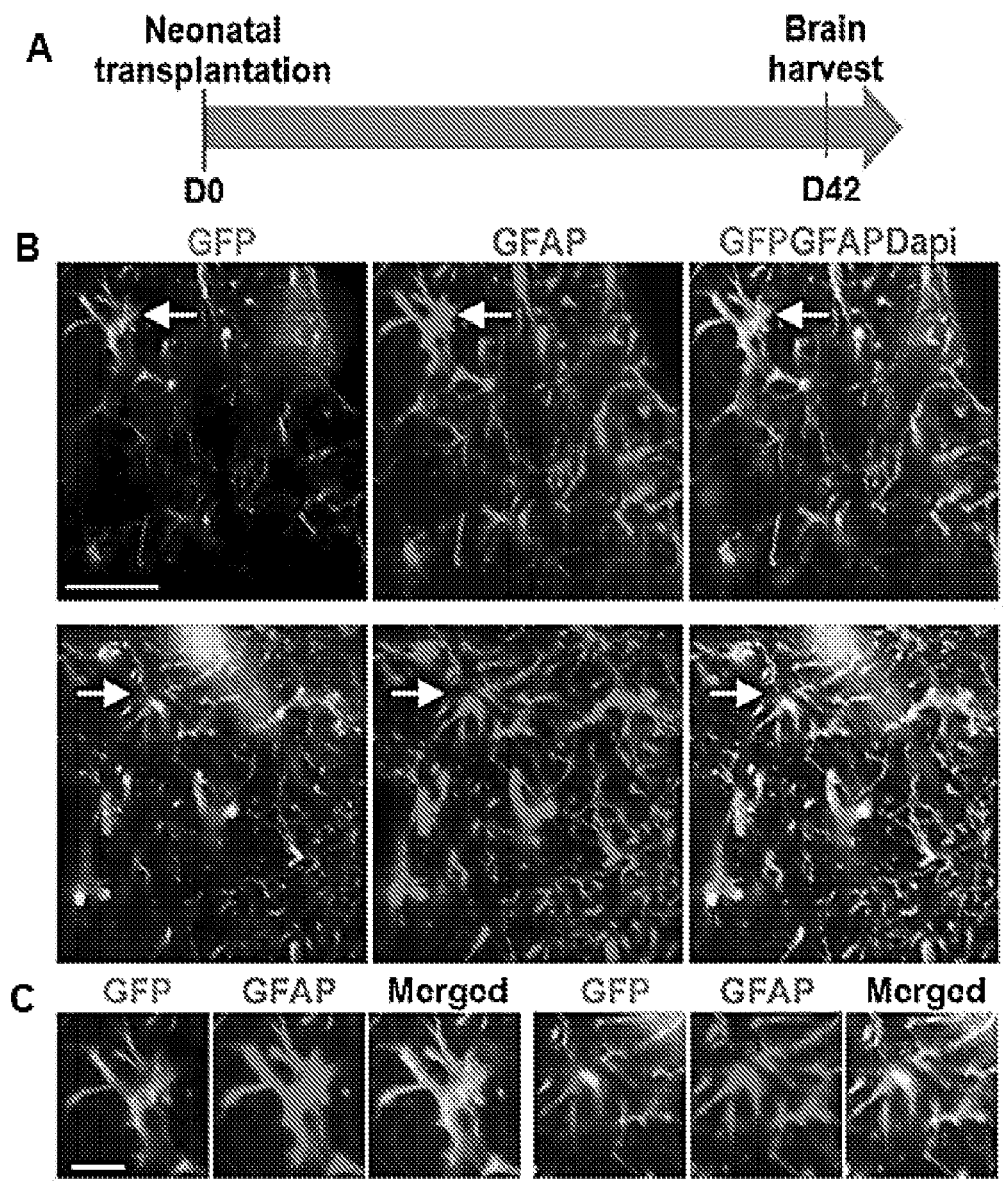
FIGS. 11A-11D illustrate VCSTO-induced astrocytes survived and maintained astrocytic marker expression in vivo.
Figure 11D:
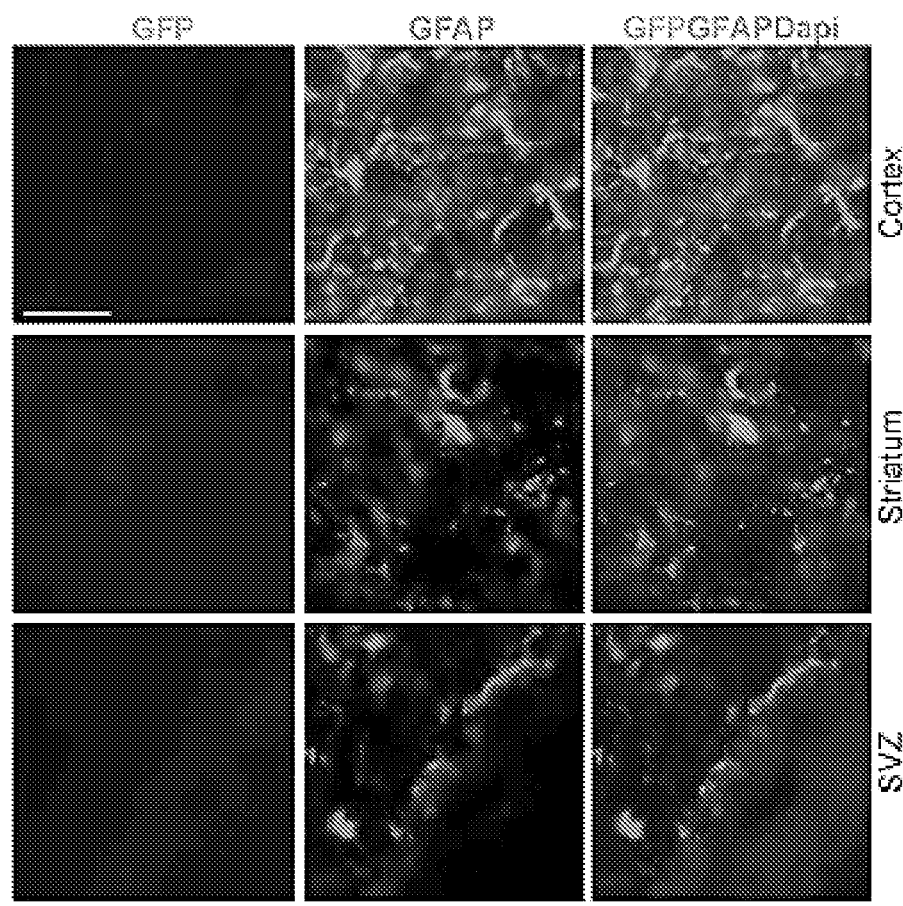

Example 7 VCSTO-Induced Astrocytes can Survive and Retain Astrocyte Identity In Vivo To determine if compound-induced astrocytes can survive and maintain their astrocytic identity in vivo, the VCSTO-induced astrocytes were labeled with a GFP reporter and transplanted into the lateral ventricles of immunodeficient neonatal NOD scid gamma (NSG) mice (FIG. 11A). Six weeks after transplantation, the grafted brains were analyzed by immunostaining. The GFP-positive grafted cells survived 6-week engraftment and continued to express GFAP in the brain (FIG. 11B, 11C). In contrast, the control MEFs were not able to survive the engraftment in the transplanted brains (FIG. 11D). These results indicate that the VCSTO-induced astrocytes can survive engraftment and maintain astrocytic marker expression in vivo.

Example 8 Compound-Induced Astrocytes can be Used to Model Neurological Disease

Figures 12A, 12B:
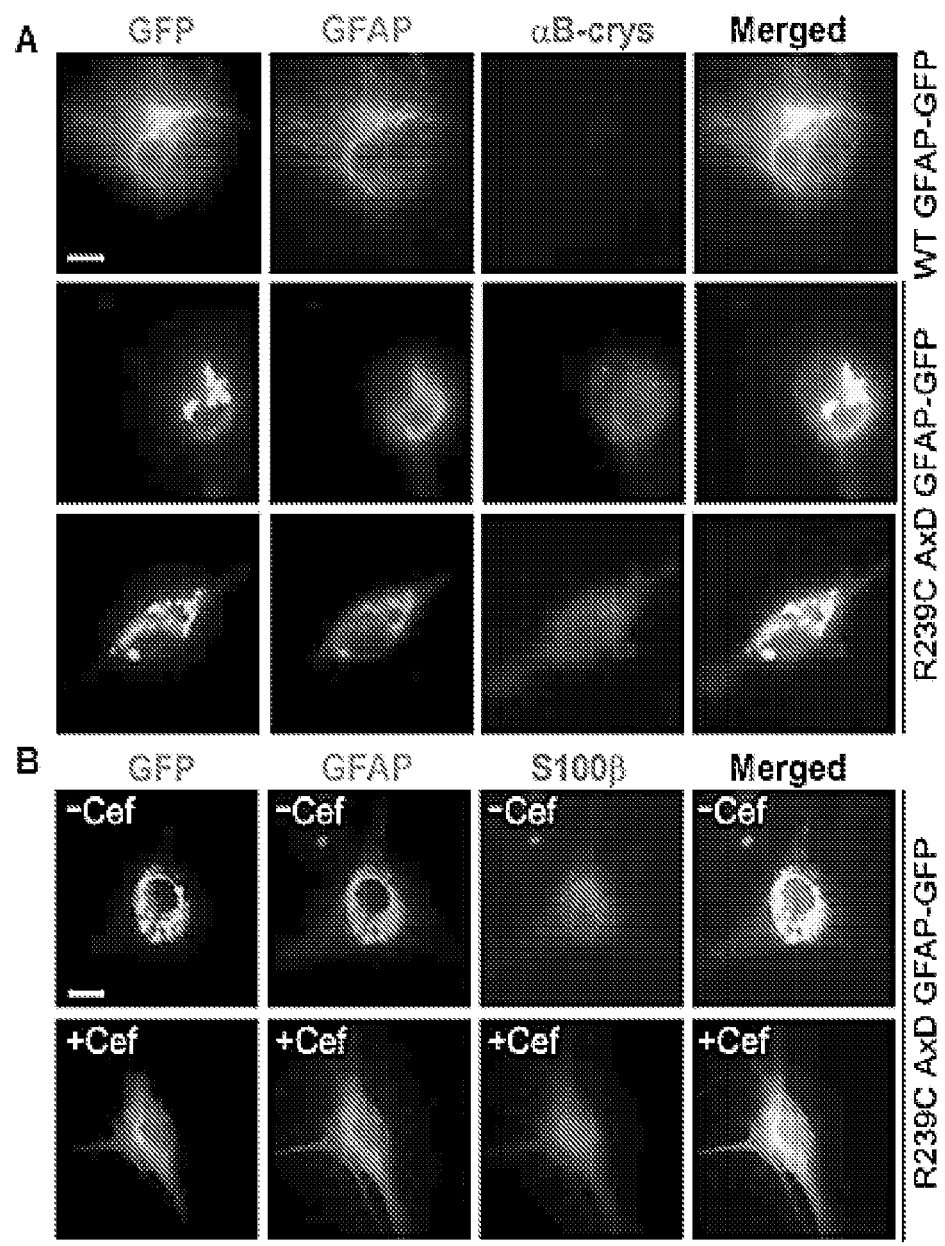
FIGS. 12A-12E illustrate recapitulating GFAP protein aggregates in VCSTO-induced astrocytes (iA) transfected with an AxD mutant GFAP.

AxD is a neurological disease with astrocyte dysfunction and is caused by genetic mutation of the GFAP gene (Messing et al., 2012). Expression of AxD mutant GFAP induces the expression of αB-crystallin, a small heat shock protein, and the formation of protein aggregates containing GFAP and αB-crystallin in astrocytes (Messing et al., 2012). The compound-induced astrocytes were tested to see if they could be used to model AxD. Plasmid expressing GFP fusion of the wild type (WT) or AxD mutant GFAP containing the R239C mutation, a hotspot mutation for AxD (Hagemann et al., 2006), were transfected into VCSTO-induced astrocytes. Expression of the AxD mutant GFAP in induced astrocytes promoted the expression of αB-crystallin and the formation of protein aggregates immunoreactive for GFAP and αB-crystallin, whereas transfection of the same amount of WT GFAP-GFP did not induce detectable αB-crystallin expression and GFAP protein aggregation (FIG. 12A). The β-lactam antibiotic ceftriaxone has been shown to facilitate the elimination of AxD mutant GFAP protein aggregates in primary astrocytes (Bachetti et al., 2010). VCSTO-induced astrocytes transfected with the AxD mutant GFAP were treated with ceftriaxone. Substantial elimination of GFAP protein aggregates was detected in ceftriaxone-treated cells, compared to vehicle control-treated cells (FIG. 12B, 12C). Although MEFs transduced with the AxD mutant GFAP also exhibited GFAP protein aggregates, the fibroblast aggregates were not responsive to ceftriaxone treatment (FIG. 12D).

Figures 12C, 12D, 12E:
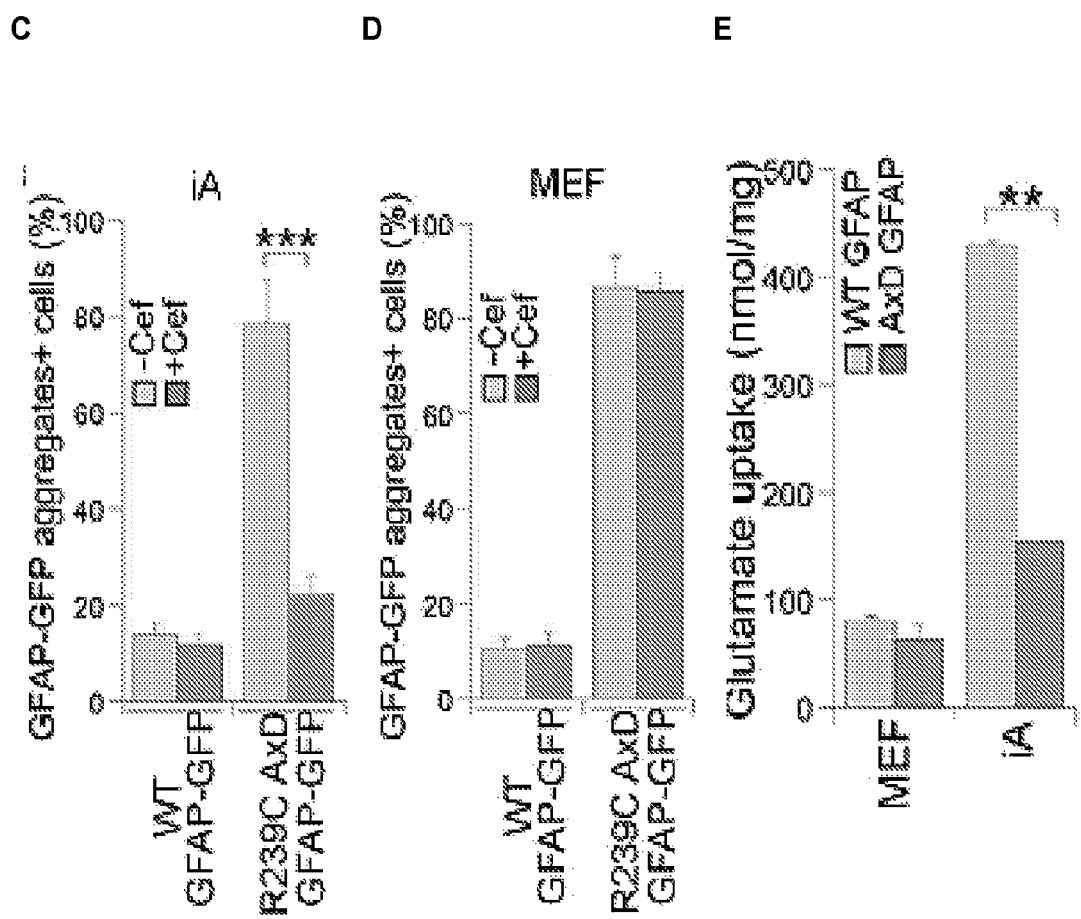

Moreover, glutamate uptake assay revealed that VCSTO-induced astrocytes transduced with the AxD mutant GFAP exhibited reduced glutamate uptake, compared to VCSTO-induced astrocytes transduced with WT GFAP (FIG. 12E). These results together suggest that compound-induced astrocytes could be used to model neurological diseases with astrocyte dysfunction and test candidate drugs for these diseases.

Example 9 VCSTO Could Induce Astrocytic Conversion from Human Fibrobasts

Figures 13A, 13B, 13C, 13D, 13E, 13F:
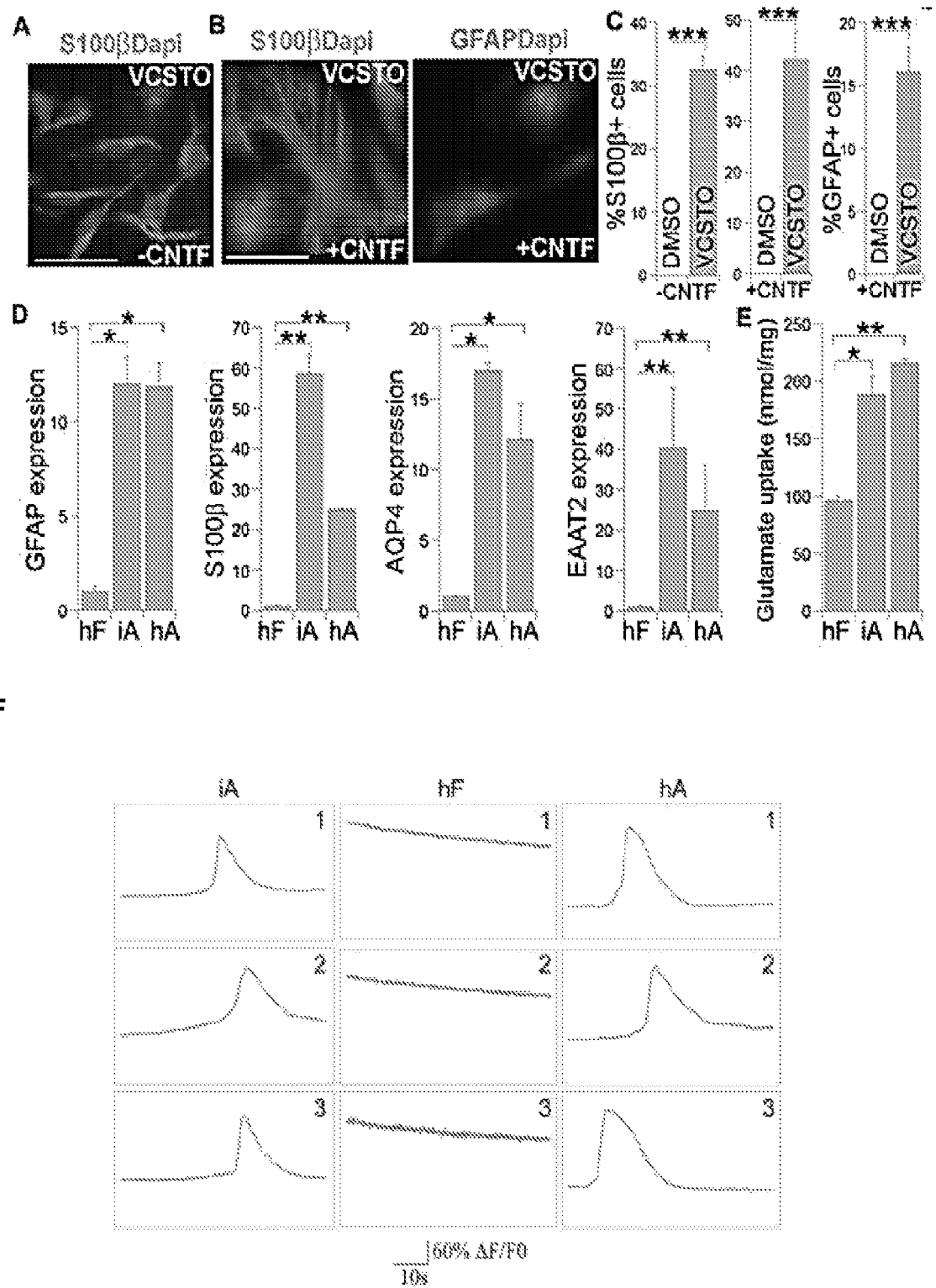
FIGS. 13A-13J illustrate reprogramming human fibroblasts into astrocytic cells by VCSTO.

To determine if human fibroblasts could be induced for astrocytic conversion using small molecule compounds, human foreskin fibroblasts were treated with VCSTO compounds. Forty days after compound treatment, a large number of cells with astroglial progenitor-like morphology were observed. Because S100β is a marker for human astroglial progenitor cells and astrocytes, the VCSTO-treated cells were stained for S100β and it was found that more than 30% of cells were S100β+ cells, whereas no S100β+ cells were detected in DMSO-treated cells (FIG. 13A, 13C). Treatment of the astroglial progenitor cells with ciliary neurotrophic factor (CNTF) for 6 days allowed the maturation of these cells into astrocytes with bigger cell body and more complex morphology. Immunostaining of the resultant cells allowed the detection of both S100β+ cells and GFAP+ cells in VCSTO-treated cells (FIG. 13B, 13C).

In a parallel experiment, robust induction of astrocyte marker genes, GFAP, S100β, AQP4 and EAAT2, was detected in VCSTO-reprogrammed cells (iA), to a level that is similar to or higher than that in human iPSC-derived astrocytes (hA) (FIG. 13D). In contrast, the expression level of the astrocytic genes is much lower in DMSO-treated human fibroblasts (hF) (FIG. 13D). Moreover, human induced astrocytes exhibited potent glutamate uptake, compared to parental fibroblasts (FIG. 13E). Calcium imaging analysis revealed that the human iA exhibited glutamate-induced calcium signal change, similar to hA, whereas parental fibroblasts did not exhibit calcium signal change in response to glutamate stimulation (FIG. 13F). These results together indicate that the VCSTO cocktail could induce human fibroblasts into astroglial progenitor cells that can be further matured into functional astrocytes.

Figure 13G:
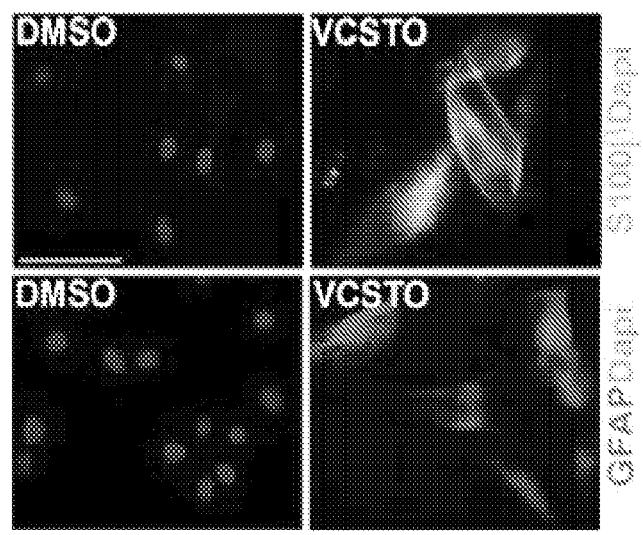
Figure 13H:
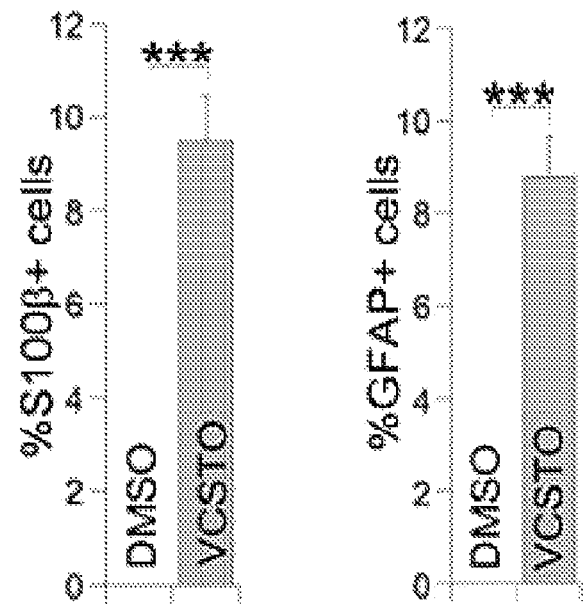
Figure 13I:
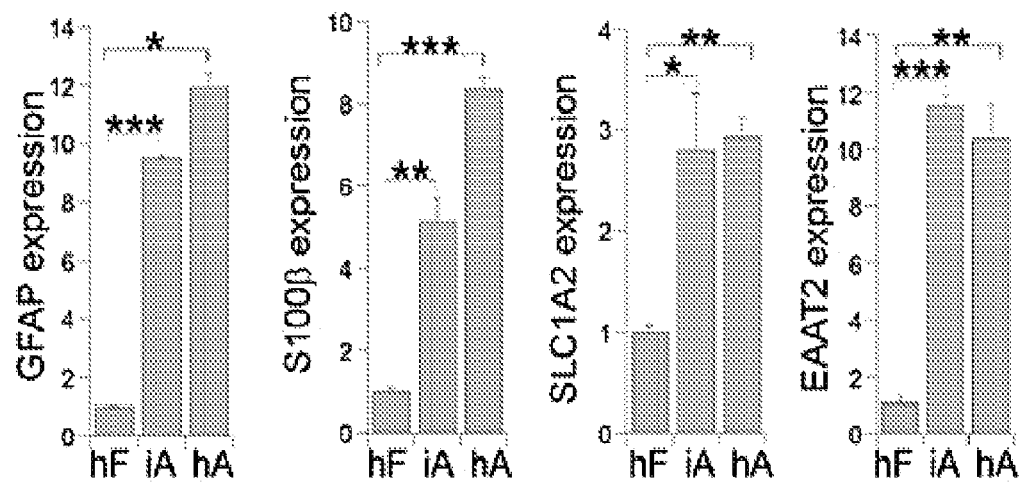
Figure 13J:
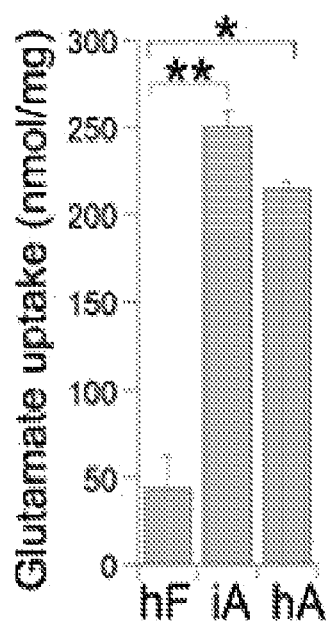

To determine if adult human fibroblasts could be induced into astrocytes using small molecules, human fibroblasts derived from a 71 year-old donor were treated with the VCSTO compounds. After forty days of VCSTO compound treatment and ten days of CNTF-induced maturation, both S100β+ cells and GFAP+ cells were detected in VCSTO-treated cells, but not in DMSO-treated cells (FIG. 13G, 13H). RT-PCR analysis revealed potent induction of astrocyte marker genes, GFAP, S100β, SLC1A2, and EAAT2 in VCSTO-induced cells, compared to that in DMSO-treated cells (FIG. 13I). The induced astrocytes also exhibited substantial glutamate uptake, compared to parental fibroblasts (FIG. 13J). These results together indicate that the VCSTO compounds could induce human adult fibroblasts into functional astrocytes.

All publications and patent documents cited herein are incorporated by reference.

REFERENCES

Bachetti, T., Caroli, F., Bocca, P., Prigione, I., Balbi, P., Biancheri, R., Filocamo, M., Mariotti, C., Pareyson, D., Ravazzolo, R., et al. (2008). Mild functional effects of a novel GFAP mutant allele identified in a familial case of adult-onset Alexander disease. EurJ Hum Genet 16, 462-470.

Bachetti, T., Di Zanni, E., Balbi, P., Bocca, P., Prigione, I., Deiana, G. A., Rezzani, A., Ceccherini, I., and Sechi, G.

(2010). In vitro treatments with ceftriaxone promote elimination of mutant glial fibrillary acidic protein and transcription down-regulation. Experimental cell research 316, 2152-2165.

Banker, G. A. (1980). Trophic interactions between astroglial cells and hippocampal neurons in culture. Science (New York, N.Y. 209, 809-810.

Barres, B. A. (2008). The mystery and magic of glia: a perspective on their roles in health and disease. Neuron 60, 430-440.

Bonaguidi, M. A., McGuire, T., Hu, M., Kan, L., Samanta, J., and Kessler, J. A. (2005). LIF and BMP signaling generate separate and discrete types of GFAP-expressing cells. Development (Cambridge, England) 132, 5503-5514.

Caiazzo, M., Dell'Anno, M. T., Dvoretskova, E., Lazarevic, D., Taverna, S., Leo, D., Sotnikova, T. D., Menegon, A., Roncaglia, P., Colciago, G., et al. (2011). Direct generation of functional dopaminergic neurons from mouse and human fibroblasts. Nature 476, 224-227.

Caiazzo, M., Giannelli, S., Valente, P., Lignani, G., Carissimo, A., Sessa, A., Colasante, G., Bartolomeo, R., Massimino, L., Ferroni, S., et al. (2015). Direct Conversion of Fibroblasts into Functional Astrocytes by Defined Transcription Factors. Stem Cell Reports.

Calone, I., Souchelnytskyi S. (2012). Inhibition of TGFβ signaling and Its Implications in Anticancer Treatments. Exp. Oncol. 34, 9-16.

Cassady, J. P., D'Alessio, A. C., Sarkar, S., Dani, V. S., Fan, Z. P., Ganz, K., Roessler, R., Sur, M., Young, R. A., and Jaenisch, R. (2014). Direct lineage conversion of adult mouse liver cells and B lymphocytes to neural stem cells. Stem Cell Reports 3, 948-956.

Chaudhry, F. A., Lehre, K. P., van Lookeren Campagne, M., Ottersen, O. P., Danbolt, N. C., and Storm-Mathisen, J. (1995). Glutamate transporters in glial plasma membranes: highly differentiated localizations revealed by quantitative ultrastructural immunocytochemistry. Neuron 15, 711-720.

Cheng, L., Hu, W., Qiu, B., Zhao, J., Yu, Y., Guan, W., Wang, M., Yang, W., and Pei, G. (2014). Generation of neural progenitor cells by chemical cocktails and hypoxia. Cell research 24, 665-679.

Davis, R. L., Weintraub, H., and Lassar, A. B. (1987). Expression of a single transfected cDNA converts fibroblasts to myoblasts. Cell 51, 987-1000.

Eroglu, C., and Barres, B. A. (2010). Regulation of synaptic connectivity by glia. Nature 468, 223-231.

Gellibert, F., Woolven, J., Fouchet, M. H., Mathews, N., Goodland, H., Lovegrove, V., Laroze, A., Nguyen, V. L., Sautet, S., Wang, R., et al. (2004). Identification of 1,5-naphthyridine derivatives as a novel series of potent and selective TGF-beta type I receptor inhibitors. Journal of medicinal chemistry 47, 4494-4506.

Gross, R. E., Mehler, M. F., Mabie, P. C., Zang, Z., Santschi, L., and Kessler, J. A. (1996). Bone morphogenetic proteins promote astroglial lineage commitment by mammalian subventricular zone progenitor cells. Neuron 17, 595-606.

Hagemann, T. L., Connor, J. X., and Messing, A. (2006). Alexander disease-associated glial fibrillary acidic protein mutations in mice induce Rosenthal fiber formation and a white matter stress response. J Neurosci 26, 11162-11173.

Hama, H., Hara, C., Yamaguchi, K., and Miyawaki, A. (2004). PKC signaling mediates global enhancement of excitatory synaptogenesis in neurons triggered by local contact with astrocytes. Neuron 41, 405-415.

Han, D. W., Tapia, N., Hermann, A., Hemmer, K., Hoing, S., Arauzo-Bravo, M. J., Zaehres, H., Wu, G., Frank, S., Moritz, S., et al. (2012). Direct reprogramming of fibroblasts into neural stem cells by defined factors. Cell stem cell 10, 465-472.

Hatada, I., Namihira, M., Morita, S., Kimura, M., Horii, T., and Nakashima, K. (2008). Astrocyte-specific genes are generally demethylated in neural precursor cells prior to astrocytic differentiation. PloS one 3, e3189.

Hawley, R. G. (2008). Does retroviral insertional mutagenesis play a role in the generation of induced pluripotent stem cells? Mol Ther 16, 1354-1355.

Hou, P., Li, Y., Zhang, X., Liu, C., Guan, J., Li, H., Zhao, T., Ye, J., Yang, W., Liu, K., et al. (2013). Pluripotent stem cells induced from mouse somatic cells by small-molecule compounds. Science (New York, N.Y. 341, 651-654.

Hu, W., Qiu, B., Guan, W., Wang, Q., Wang, M., Li, W., Gao, L., Shen, L., Huang, Y., Xie, G., et al. (2015). Direct Conversion of Normal and Alzheimer's Disease Human Fibroblasts into Neuronal Cells by Small Molecules. Cell stem cell 17, 204-212.

Ichida, J. K., Blanchard, J., Lam, K., Son, E. Y., Chung, J. E., Egli, D., Loh, K. M., Carter, A. C., Di Giorgio, F. P., Koszka, K., et al. (2009). A small-molecule inhibitor of tgf-Beta signaling replaces sox2 in reprogramming by inducing nanog. Cell stem cell 5, 491-503.

Inman, G. J., Nicolas, F. J., Callahan, J. F., Harling, J. D., Gaster, L. M., Reith, A. D., Laping, N. J., and Hill, C. S. (2002). SB-431542 is a potent and specific inhibitor of transforming growth factor-beta superfamily type I activin receptor-like kinase (ALK) receptors ALK4, ALK5, and ALK7. Mol Pharmacol 62, 65-74.

Irizarry, R. A., Hobbs, B., Collin, F., Beazer-Barclay, Y. D., Antonellis, K. J., Scherf, U., and Speed, T. P. (2003). Exploration, normalization, and summaries of high density oligonucleotide array probe level data. Biostatistics 4, 249-264.

Kim, J., Efe, J. A., Zhu, S., Talantova, M., Yuan, X., Wang, S., Lipton, S. A., Zhang, K., and Ding, S. (2011). Direct reprogramming of mouse fibroblasts to neural progenitors. Proceedings of the National Academy of Sciences of the United States of America 108, 7838-7843.

Kohyama, J., Sanosaka, T., Tokunaga, A., Takatsuka, E., Tsujimura, K., Okano, H., and Nakashima, K. (2010). BMP-induced REST regulates the establishment and maintenance of astrocytic identity. The Journal of cell biology 189, 159-170.

Li, W., Tian, E., Chen, Z. X., Sun, G., Ye, P., Yang, S., Lu, D., Xie, J., Ho, T. V., Tsark, W. M., et al. (2012). Identification of Oct4-activating compounds that enhance reprogramming efficiency. Proceedings of the National Academy of Sciences of the United States of America 109, 20853-20858.

Li, X., Zuo, X., Jing, J., Ma, Y., Wang, J., Liu, D., Zhu, J., Du, X., Xiong, L., Du, Y., et al. (2015). Small-Molecule-Driven Direct Reprogramming of Mouse Fibroblasts into Functional Neurons. Cell stem cell 17, 195-203.

Lin, T., Ambasudhan, R., Yuan, X., Li, W., Hilcove, S., Abujarour, R., Lin, X., Hahm, H. S., Hao, E., Hayek, A., et al. (2009). A chemical platform for improved induction of human iPSCs. Nature methods 6, 805-808.

Lujan, E., Chanda, S., Ahlenius, H., Sudhof, T. C., and Wernig, M. (2012). Direct conversion of mouse fibroblasts to self-renewing, tripotent neural precursor cells. Proceedings of the National Academy of Sciences of the United States of America 109, 2527-2532.

Maherali, N., and Hochedlinger, K. (2009). Tgfbeta signal inhibition cooperates in the induction of iPSCs and replaces Sox2 and cMyc. Curr Biol 19, 1718-1723.

Messing, A., Brenner, M., Feany, M. B., Nedergaard, M., and Goldman, J. E. (2012). Alexander Disease. J Neurosci 32, 5017-5023.

Molofsky, A. V., Krencik, R., Ullian, E. M., Tsai, H. H., Deneen, B., Richardson, W. D., Barres, B. A., and Rowitch, D. H. (2012). Astrocytes and disease: a neurodevelopmental perspective. Genes & development 26, 891-907.

Najm, F. J., Lager, A. M., Zaremba, A., Wyatt, K., Caprariello, A. V., Factor, D. C., Karl, R. T., Maeda, T., Miller, R. H., and Tesar, P. J. (2013). Transcription factor-mediated reprogramming of fibroblasts to expandable, myelinogenic oligodendrocyte progenitor cells. Nature biotechnology 31, 426-433.

Okita, K., Nakagawa, M., Hyenjong, H., Ichisaka, T., and Yamanaka, S. (2008). Generation of mouse induced pluripotent stem cells without viral vectors. Science (New York, N.Y. 322, 949-953.

Pang, Z. P., Yang, N., Vierbuchen, T., Ostermeier, A., Fuentes, D. R., Yang, T. Q., Citri, A., Sebastiano, V., Marro, S., Sudhof, T. C., et al. (2011). Induction of human neuronal cells by defined transcription factors. Nature 476, 220-223.

Rajan, P., and McKay, R. D. (1998). Multiple routes to astrocytic differentiation in the CNS. J Neurosci 18, 3620-3629.

Ring, K. L., Tong, L. M., Balestra, M. E., Javier, R., Andrews-Zwilling, Y., Li, G., Walker, D., Zhang, W. R., Kreitzer, A. C., and Huang, Y. (2012). Direct reprogramming of mouse and human fibroblasts into multipotent neural stem cells with a single factor. Cell stem cell 11, 100-109.

Schildge, S., Bohrer, C., Beck, K., and Schachtrup, C. (2013). Isolation and culture of mouse cortical astrocytes. J Vis Exp doi: 10.3791/50079.

Simard, M., and Nedergaard, M. (2004). The neurobiology of glia in the context of water and ion homeostasis. Neuroscience 129, 877-896.

Smith, J. R., Vallier, L., Lupo, G., Alexander, M., Harris, W. A., and Pedersen, R. A. (2008). Inhibition of Activin/Nodal signaling promotes specification of human embryonic stem cells into neuroectoderm. Developmental biology 313, 107-117.

Sofroniew, M. V., and Vinters, H. V. (2010). Astrocytes: biology and pathology. Acta neuropathologica 119, 7-35.

Song, H., Stevens, C. F., and Gage, F. H. (2002). Astroglia induce neurogenesis from adult neural stem cells. Nature 417, 39-44.

Szabo, P. E., Hubner, K., Scholer, H., and Mann, J. R. (2002). Allele-specific expression of imprinted genes in mouse migratory primordial germ cells. Mechanisms of development 115, 157-160.

Takahashi, K., and Yamanaka, S. (2006). Induction of pluripotent stem cells from mouse embryonic and adult fibroblast cultures by defined factors. Cell 126, 663-676.

Thier, M., Worsdorfer, P., Lakes, Y. B., Gorris, R., Herms, S., Opitz, T., Seiferling, D., Quandel, T., Hoffmann, P., Nothen, M. M., et al. (2012). Direct conversion of fibroblasts into stably expandable neural stem cells. Cell stem cell 10, 473-479.

Tojo, M., Hamashima, Y., Hanyu, A., Kajimoto, T., Saitoh, M., Miyazono, K., Node, M., and Imamura, T. (2005). The ALK-5 inhibitor A-83-01 inhibits Smad signaling and epithelial-to-mesenchymal transition by transforming growth factor-beta. Cancer Sci 96, 791-800.

Verkhratsky, A., Sofroniew, M. V., Messing, A., Delanerolle, N. C., Rempe, D., Rodriguez Arellano, J. J., and Nedergaard, M. (2012). Neurological diseases as primary gliopathies: A reassessment of neurocentrism. ASN neuro doi: 10.1042/AN20120010.

Vierbuchen, T., Ostermeier, A., Pang, Z. P., Kokubu, Y., Sudhof, T. C., and Wernig, M. (2010). Direct conversion of fibroblasts to functional neurons by defined factors. Nature 463, 1035-1041.

Wang, D. D., and Bordey, A. (2008). The astrocyte odyssey. Progress in neurobiology 86, 342-367.

Xu, R. H., Sampsell-Barron, T. L., Gu, F., Root, S., Peck, R. M., Pan, G., Yu, J., Antosiewicz-Bourget, J., Tian, S., Stewart, R., et al. (2008). NANOG is a direct target of TGFbeta/activin-mediated SMAD signaling in human ESCs. Cell stem cell 3, 196-206.

Yang, N., Zuchero, J. B., Ahlenius, H., Marro, S., Ng, Y. H., Vierbuchen, T., Hawkins, J. S., Geissler, R., Barres, B. A., and Wernig, M. (2013). Generation of oligodendroglial cells by direct lineage conversion. Nature biotechnology 31, 434-439.

Yoo, A. S., Sun, A. X., Li, L., Shcheglovitov, A., Portmann, T., Li, Y., Lee-Messer, C., Dolmetsch, R. E., Tsien, R. W., and Crabtree, G. R. (2011). MicroRNA-mediated conversion of human fibroblasts to neurons. Nature 476, 228-231.

Zhang, L., Yin, J. C., Yeh, H., Ma, N. X., Lee, G., Chen, X. A., Wang, Y., Lin, L., Chen, L., Jin, P., et al. (2015). Small Molecules Efficiently Reprogram Human Astroglial Cells into Functional Neurons. Cell stem cell 17, 735-747.

Zhuo, L., Sun, B., Zhang, C. L., Fine, A., Chiu, S. Y., and Messing, A. (1997). Live astrocytes visualized by green fluorescent protein in transgenic mice. Developmental biology 187, 36-42.

The invention claimed is:

1. A method of reprogramming or converting somatic tissue or cells directly into astrocytes or astroglial progenitor cells, comprising contacting the somatic tissue or cells with one or more small molecules to obtain astrocytes or astroglial progenitor cells, wherein the one or more small molecules include at least one TGF-β inhibitor, and wherein the one or more small molecules are a combination of VPA (V), CHIR99021 (C), 616452 (6), tranylcypromine (T), and OAC1 (O), a combination of VPA (V), CHIR99021 (C), A-83-01 (A), tranylcypromine (T), and OAC1 (O), or a combination of VPA (V), CHIR99021 (C), SB-431542 (S), tranylcypromine (T), and OAC1 (O).

2. The method of claim 1, wherein the somatic tissue or cells are autologous tissue or cells.

3. The method of claim 1, wherein the somatic tissue or cells are human somatic tissue or cells.

4. The method of claim 1, wherein the somatic tissue or cells are fibroblasts, urinary cells or blood cells.

5. The method of claim 1, wherein the astrocytes or astroglial progenitor cells contain both anterior and posterior subtypes.

* * * * *

SEQUENCE LISTING

<160> NUMBER OF SEQ ID NOS: 74

<210> SEQ ID NO 1
<211> LENGTH: 21
<212> TYPE: DNA
<213> ORGANISM: Artificial Sequence
<220> FEATURE:
<223> OTHER INFORMATION: Synthetic primer

<400> SEQUENCE: 1
gaagttcgag aactccggga g                                                 21

```
<210> SEQ ID NO 2
<211> LENGTH: 22
<212> TYPE: DNA
<213> ORGANISM: Artificial Sequence
<220> FEATURE:
<223> OTHER INFORMATION: Synthetic primer

<400> SEQUENCE: 2
ttagaccgat accactcctc tg                                              22

<210> SEQ ID NO 3
<211> LENGTH: 22
<212> TYPE: DNA
<213> ORGANISM: Artificial Sequence
<220> FEATURE:
<223> OTHER INFORMATION: Synthetic primer

<400> SEQUENCE: 3
ccctcattga tgtcttccac ca                                              22

<210> SEQ ID NO 4
<211> LENGTH: 22
<212> TYPE: DNA
<213> ORGANISM: Artificial Sequence
<220> FEATURE:
<223> OTHER INFORMATION: Synthetic primer

<400> SEQUENCE: 4
cttcgtccag cgtctccatc ac                                              22

<210> SEQ ID NO 5
<211> LENGTH: 20
<212> TYPE: DNA
<213> ORGANISM: Artificial Sequence
<220> FEATURE:
<223> OTHER INFORMATION: Synthetic primer

<400> SEQUENCE: 5
ggaagacagc agcctgcctg                                                 20

<210> SEQ ID NO 6
<211> LENGTH: 20
<212> TYPE: DNA
<213> ORGANISM: Artificial Sequence
<220> FEATURE:
<223> OTHER INFORMATION: Synthetic primer

<400> SEQUENCE: 6
cttcacatta ctcagggcac                                                 20

<210> SEQ ID NO 7
<211> LENGTH: 20
<212> TYPE: DNA
<213> ORGANISM: Artificial Sequence
<220> FEATURE:
<223> OTHER INFORMATION: Synthetic primer

<400> SEQUENCE: 7
acaggtgggg ttcctcaatc                                                 20

<210> SEQ ID NO 8
<211> LENGTH: 20
<212> TYPE: DNA
<213> ORGANISM: Artificial Sequence
<220> FEATURE:
<223> OTHER INFORMATION: Synthetic primer
```

<400> SEQUENCE: 8
gaggcttggt gtctggcatg                                         20

<210> SEQ ID NO 9
<211> LENGTH: 20
<212> TYPE: DNA
<213> ORGANISM: Artificial Sequence
<220> FEATURE:
<223> OTHER INFORMATION: Synthetic primer

<400> SEQUENCE: 9
ggagaaggtc acggagatcg                                         20

<210> SEQ ID NO 10
<211> LENGTH: 20
<212> TYPE: DNA
<213> ORGANISM: Artificial Sequence
<220> FEATURE:
<223> OTHER INFORMATION: Synthetic primer

<400> SEQUENCE: 10
tgaagtcctc cacatgctcc                                         20

<210> SEQ ID NO 11
<211> LENGTH: 20
<212> TYPE: DNA
<213> ORGANISM: Artificial Sequence
<220> FEATURE:
<223> OTHER INFORMATION: Synthetic primer

<400> SEQUENCE: 11
tggactctca acgctgcatg                                         20

<210> SEQ ID NO 12
<211> LENGTH: 20
<212> TYPE: DNA
<213> ORGANISM: Artificial Sequence
<220> FEATURE:
<223> OTHER INFORMATION: Synthetic primer

<400> SEQUENCE: 12
ggacagtgct gaaggacacc                                         20

<210> SEQ ID NO 13
<211> LENGTH: 20
<212> TYPE: DNA
<213> ORGANISM: Artificial Sequence
<220> FEATURE:
<223> OTHER INFORMATION: Synthetic primer

<400> SEQUENCE: 13
ggagttcatc atggagagtg                                         20

<210> SEQ ID NO 14
<211> LENGTH: 20
<212> TYPE: DNA
<213> ORGANISM: Artificial Sequence
<220> FEATURE:
<223> OTHER INFORMATION: Synthetic primer

<400> SEQUENCE: 14
cattccagtg cagtagttgg                                         20

<210> SEQ ID NO 15
<211> LENGTH: 20

<212> TYPE: DNA
<213> ORGANISM: Artificial Sequence
<220> FEATURE:
<223> OTHER INFORMATION: Synthetic primer

<400> SEQUENCE: 15
cttgccgatg tggtggatac                                           20

<210> SEQ ID NO 16
<211> LENGTH: 20
<212> TYPE: DNA
<213> ORGANISM: Artificial Sequence
<220> FEATURE:
<223> OTHER INFORMATION: Synthetic primer

<400> SEQUENCE: 16
ctctgcaagg ctctcaggtg                                           20

<210> SEQ ID NO 17
<211> LENGTH: 20
<212> TYPE: DNA
<213> ORGANISM: Artificial Sequence
<220> FEATURE:
<223> OTHER INFORMATION: Synthetic primer

<400> SEQUENCE: 17
tcacttgctc attctccctt                                           20

<210> SEQ ID NO 18
<211> LENGTH: 18
<212> TYPE: DNA
<213> ORGANISM: Artificial Sequence
<220> FEATURE:
<223> OTHER INFORMATION: Synthetic primer

<400> SEQUENCE: 18
gacctctcca ttcctggc                                             18

<210> SEQ ID NO 19
<211> LENGTH: 34
<212> TYPE: DNA
<213> ORGANISM: Artificial Sequence
<220> FEATURE:
<223> OTHER INFORMATION: Synthetic primer

<400> SEQUENCE: 19
tcgactcgag ccctctcact gaacctctgt ctcc                           34

<210> SEQ ID NO 20
<211> LENGTH: 39
<212> TYPE: DNA
<213> ORGANISM: Artificial Sequence
<220> FEATURE:
<223> OTHER INFORMATION: Synthetic primer

<400> SEQUENCE: 20
gcgaattctt aattaaaaac cacccaatct gtggctcca                      39

<210> SEQ ID NO 21
<211> LENGTH: 20
<212> TYPE: DNA
<213> ORGANISM: Artificial Sequence
<220> FEATURE:
<223> OTHER INFORMATION: Synthetic primer

```
<400> SEQUENCE: 21
aggagttgat gagcagcttg                                              20

<210> SEQ ID NO 22
<211> LENGTH: 20
<212> TYPE: DNA
<213> ORGANISM: Artificial Sequence
<220> FEATURE:
<223> OTHER INFORMATION: Synthetic primer

<400> SEQUENCE: 22
ggtcacgaac attgagcgtg                                              20

<210> SEQ ID NO 23
<211> LENGTH: 20
<212> TYPE: DNA
<213> ORGANISM: Artificial Sequence
<220> FEATURE:
<223> OTHER INFORMATION: Synthetic primer

<400> SEQUENCE: 23
tcttgaacgt gtggctaacc                                              20

<210> SEQ ID NO 24
<211> LENGTH: 20
<212> TYPE: DNA
<213> ORGANISM: Artificial Sequence
<220> FEATURE:
<223> OTHER INFORMATION: Synthetic primer

<400> SEQUENCE: 24
tctccagagc acttgcatgg                                              20

<210> SEQ ID NO 25
<211> LENGTH: 18
<212> TYPE: DNA
<213> ORGANISM: Artificial Sequence
<220> FEATURE:
<223> OTHER INFORMATION: Synthetic primer

<400> SEQUENCE: 25
gcccacagcc ttctacac                                                18

<210> SEQ ID NO 26
<211> LENGTH: 18
<212> TYPE: DNA
<213> ORGANISM: Artificial Sequence
<220> FEATURE:
<223> OTHER INFORMATION: Synthetic primer

<400> SEQUENCE: 26
ccagggtcac catttctc                                                18

<210> SEQ ID NO 27
<211> LENGTH: 21
<212> TYPE: DNA
<213> ORGANISM: Artificial Sequence
<220> FEATURE:
<223> OTHER INFORMATION: Synthetic primer

<400> SEQUENCE: 27
gcaacagtcg cttcacctac a                                            21

<210> SEQ ID NO 28
```

<211> LENGTH: 21
<212> TYPE: DNA
<213> ORGANISM: Artificial Sequence
<220> FEATURE:
<223> OTHER INFORMATION: Synthetic primer

<400> SEQUENCE: 28
caatgtccaa gggagccaca t                                              21

<210> SEQ ID NO 29
<211> LENGTH: 20
<212> TYPE: DNA
<213> ORGANISM: Artificial Sequence
<220> FEATURE:
<223> OTHER INFORMATION: Synthetic primer

<400> SEQUENCE: 29
aatcctggtg atgtccgacc                                                20

<210> SEQ ID NO 30
<211> LENGTH: 20
<212> TYPE: DNA
<213> ORGANISM: Artificial Sequence
<220> FEATURE:
<223> OTHER INFORMATION: Synthetic primer

<400> SEQUENCE: 30
caaagttcca ccgttctcgg                                                20

<210> SEQ ID NO 31
<211> LENGTH: 22
<212> TYPE: DNA
<213> ORGANISM: Artificial Sequence
<220> FEATURE:
<223> OTHER INFORMATION: Synthetic primer

<400> SEQUENCE: 31
gagcttcctg aacagcgaag tg                                             22

<210> SEQ ID NO 32
<211> LENGTH: 22
<212> TYPE: DNA
<213> ORGANISM: Artificial Sequence
<220> FEATURE:
<223> OTHER INFORMATION: Synthetic primer

<400> SEQUENCE: 32
tggccacctc cagatagtca tc                                             22

<210> SEQ ID NO 33
<211> LENGTH: 20
<212> TYPE: DNA
<213> ORGANISM: Artificial Sequence
<220> FEATURE:
<223> OTHER INFORMATION: Synthetic primer

<400> SEQUENCE: 33
gcctgactcg tcagacaatc                                                20

<210> SEQ ID NO 34
<211> LENGTH: 20
<212> TYPE: DNA
<213> ORGANISM: Artificial Sequence
<220> FEATURE:
<223> OTHER INFORMATION: Synthetic primer

<400> SEQUENCE: 34
cgtctgctcc acagtgccag                                                         20

<210> SEQ ID NO 35
<211> LENGTH: 20
<212> TYPE: DNA
<213> ORGANISM: Artificial Sequence
<220> FEATURE:
<223> OTHER INFORMATION: Synthetic primer

<400> SEQUENCE: 35
tgagcttcaa cagcatcacc                                                         20

<210> SEQ ID NO 36
<211> LENGTH: 20
<212> TYPE: DNA
<213> ORGANISM: Artificial Sequence
<220> FEATURE:
<223> OTHER INFORMATION: Synthetic primer

<400> SEQUENCE: 36
aagtcatttt gcccaactgc                                                         20

<210> SEQ ID NO 37
<211> LENGTH: 20
<212> TYPE: DNA
<213> ORGANISM: Artificial Sequence
<220> FEATURE:
<223> OTHER INFORMATION: Synthetic primer

<400> SEQUENCE: 37
cctggccata gacgaagaag                                                         20

<210> SEQ ID NO 38
<211> LENGTH: 20
<212> TYPE: DNA
<213> ORGANISM: Artificial Sequence
<220> FEATURE:
<223> OTHER INFORMATION: Synthetic primer

<400> SEQUENCE: 38
agcctctgca tgcctgatac                                                         20

<210> SEQ ID NO 39
<211> LENGTH: 20
<212> TYPE: DNA
<213> ORGANISM: Artificial Sequence
<220> FEATURE:
<223> OTHER INFORMATION: Synthetic primer

<400> SEQUENCE: 39
acaggcagct cttgaaggtc                                                         20

<210> SEQ ID NO 40
<211> LENGTH: 20
<212> TYPE: DNA
<213> ORGANISM: Artificial Sequence
<220> FEATURE:
<223> OTHER INFORMATION: Synthetic primer

<400> SEQUENCE: 40
agacagcgct caatgctatc                                                         20

<210> SEQ ID NO 41

<211> LENGTH: 24
<212> TYPE: DNA
<213> ORGANISM: Artificial Sequence
<220> FEATURE:
<223> OTHER INFORMATION: Synthetic primer

<400> SEQUENCE: 41
gcctctgtgg ctcctgcaat aaac                                           24

<210> SEQ ID NO 42
<211> LENGTH: 23
<212> TYPE: DNA
<213> ORGANISM: Artificial Sequence
<220> FEATURE:
<223> OTHER INFORMATION: Synthetic primer

<400> SEQUENCE: 42
cttctcgaag aagctgctgc ctc                                            23

<210> SEQ ID NO 43
<211> LENGTH: 20
<212> TYPE: DNA
<213> ORGANISM: Artificial Sequence
<220> FEATURE:
<223> OTHER INFORMATION: Synthetic primer

<400> SEQUENCE: 43
ccaagtcacc ctaccagctg                                                20

<210> SEQ ID NO 44
<211> LENGTH: 20
<212> TYPE: DNA
<213> ORGANISM: Artificial Sequence
<220> FEATURE:
<223> OTHER INFORMATION: Synthetic primer

<400> SEQUENCE: 44
tcctctggta ccactgcttg                                                20

<210> SEQ ID NO 45
<211> LENGTH: 20
<212> TYPE: DNA
<213> ORGANISM: Artificial Sequence
<220> FEATURE:
<223> OTHER INFORMATION: Synthetic primer

<400> SEQUENCE: 45
gctgctgctg ctgtctgaac                                                20

<210> SEQ ID NO 46
<211> LENGTH: 20
<212> TYPE: DNA
<213> ORGANISM: Artificial Sequence
<220> FEATURE:
<223> OTHER INFORMATION: Synthetic primer

<400> SEQUENCE: 46
acatccctgc tcactctctg                                                20

<210> SEQ ID NO 47
<211> LENGTH: 19
<212> TYPE: DNA
<213> ORGANISM: Artificial Sequence
<220> FEATURE:
<223> OTHER INFORMATION: Synthetic primer

```
<400> SEQUENCE: 47
tggcaacact gcccattca                                              19

<210> SEQ ID NO 48
<211> LENGTH: 21
<212> TYPE: DNA
<213> ORGANISM: Artificial Sequence
<220> FEATURE:
<223> OTHER INFORMATION: Synthetic primer

<400> SEQUENCE: 48
gcatttgcgc aacacaggtt a                                           21

<210> SEQ ID NO 49
<211> LENGTH: 20
<212> TYPE: DNA
<213> ORGANISM: Artificial Sequence
<220> FEATURE:
<223> OTHER INFORMATION: Synthetic primer

<400> SEQUENCE: 49
ttcacgtgag cacggtaaac                                             20

<210> SEQ ID NO 50
<211> LENGTH: 20
<212> TYPE: DNA
<213> ORGANISM: Artificial Sequence
<220> FEATURE:
<223> OTHER INFORMATION: Synthetic primer

<400> SEQUENCE: 50
cacttcatgc gccgattctg                                             20

<210> SEQ ID NO 51
<211> LENGTH: 19
<212> TYPE: DNA
<213> ORGANISM: Artificial Sequence
<220> FEATURE:
<223> OTHER INFORMATION: Synthetic primer

<400> SEQUENCE: 51
aaaactgcgg ggatctgag                                              19

<210> SEQ ID NO 52
<211> LENGTH: 20
<212> TYPE: DNA
<213> ORGANISM: Artificial Sequence
<220> FEATURE:
<223> OTHER INFORMATION: Synthetic primer

<400> SEQUENCE: 52
tgctttggac tcatcgacat                                             20

<210> SEQ ID NO 53
<211> LENGTH: 23
<212> TYPE: DNA
<213> ORGANISM: Artificial Sequence
<220> FEATURE:
<223> OTHER INFORMATION: Synthetic primer

<400> SEQUENCE: 53
actacccaga catttacacc agg                                         23

<210> SEQ ID NO 54
```

```
<211> LENGTH: 24
<212> TYPE: DNA
<213> ORGANISM: Artificial Sequence
<220> FEATURE:
<223> OTHER INFORMATION: Synthetic primer

<400> SEQUENCE: 54
aatgagatgg ttgaaagcca tcag                                      24

<210> SEQ ID NO 55
<211> LENGTH: 20
<212> TYPE: DNA
<213> ORGANISM: Artificial Sequence
<220> FEATURE:
<223> OTHER INFORMATION: Synthetic primer

<400> SEQUENCE: 55
ccaagagact gcgcgcgctg                                           20

<210> SEQ ID NO 56
<211> LENGTH: 20
<212> TYPE: DNA
<213> ORGANISM: Artificial Sequence
<220> FEATURE:
<223> OTHER INFORMATION: Synthetic primer

<400> SEQUENCE: 56
tgagcagcgt cttggtcttg                                           20

<210> SEQ ID NO 57
<211> LENGTH: 20
<212> TYPE: DNA
<213> ORGANISM: Artificial Sequence
<220> FEATURE:
<223> OTHER INFORMATION: Synthetic primer

<400> SEQUENCE: 57
accaaagggt catcgcgccc                                           20

<210> SEQ ID NO 58
<211> LENGTH: 20
<212> TYPE: DNA
<213> ORGANISM: Artificial Sequence
<220> FEATURE:
<223> OTHER INFORMATION: Synthetic primer

<400> SEQUENCE: 58
tggcagtcct tgcgatcggc                                           20

<210> SEQ ID NO 59
<211> LENGTH: 20
<212> TYPE: DNA
<213> ORGANISM: Artificial Sequence
<220> FEATURE:
<223> OTHER INFORMATION: Synthetic primer

<400> SEQUENCE: 59
taggtgagcc gtctttccac                                           20

<210> SEQ ID NO 60
<211> LENGTH: 20
<212> TYPE: DNA
<213> ORGANISM: Artificial Sequence
<220> FEATURE:
<223> OTHER INFORMATION: Synthetic primer
```

```
<400> SEQUENCE: 60
gcttagccag gttcgaggat                                                   20

<210> SEQ ID NO 61
<211> LENGTH: 20
<212> TYPE: DNA
<213> ORGANISM: Artificial Sequence
<220> FEATURE:
<223> OTHER INFORMATION: Synthetic primer

<400> SEQUENCE: 61
caggagtttg agggtagctc                                                   20

<210> SEQ ID NO 62
<211> LENGTH: 20
<212> TYPE: DNA
<213> ORGANISM: Artificial Sequence
<220> FEATURE:
<223> OTHER INFORMATION: Synthetic primer

<400> SEQUENCE: 62
cggttcatca tggtacagtc                                                   20

<210> SEQ ID NO 63
<211> LENGTH: 21
<212> TYPE: DNA
<213> ORGANISM: Artificial Sequence
<220> FEATURE:
<223> OTHER INFORMATION: Synthetic primer

<400> SEQUENCE: 63
ttctcttcgg tgctaggaaa c                                                 21

<210> SEQ ID NO 64
<211> LENGTH: 21
<212> TYPE: DNA
<213> ORGANISM: Artificial Sequence
<220> FEATURE:
<223> OTHER INFORMATION: Synthetic primer

<400> SEQUENCE: 64
aggaagctta tgtctctggt g                                                 21

<210> SEQ ID NO 65
<211> LENGTH: 20
<212> TYPE: DNA
<213> ORGANISM: Artificial Sequence
<220> FEATURE:
<223> OTHER INFORMATION: Synthetic primer

<400> SEQUENCE: 65
ctagttgtct tctccatgtg                                                   20

<210> SEQ ID NO 66
<211> LENGTH: 20
<212> TYPE: DNA
<213> ORGANISM: Artificial Sequence
<220> FEATURE:
<223> OTHER INFORMATION: Synthetic primer

<400> SEQUENCE: 66
aggagaggca ggacgatgac                                                   20

<210> SEQ ID NO 67
```

```
<211> LENGTH: 20
<212> TYPE: DNA
<213> ORGANISM: Artificial Sequence
<220> FEATURE:
<223> OTHER INFORMATION: Synthetic primer

<400> SEQUENCE: 67
gcgcatgtgc gacaagctgg                                              20

<210> SEQ ID NO 68
<211> LENGTH: 20
<212> TYPE: DNA
<213> ORGANISM: Artificial Sequence
<220> FEATURE:
<223> OTHER INFORMATION: Synthetic primer

<400> SEQUENCE: 68
gcgatgccaa gcgaagcagc                                              20

<210> SEQ ID NO 69
<211> LENGTH: 19
<212> TYPE: DNA
<213> ORGANISM: Artificial Sequence
<220> FEATURE:
<223> OTHER INFORMATION: Synthetic primer

<400> SEQUENCE: 69
tggtgctgat gggcaagaa                                               19

<210> SEQ ID NO 70
<211> LENGTH: 19
<212> TYPE: DNA
<213> ORGANISM: Artificial Sequence
<220> FEATURE:
<223> OTHER INFORMATION: Synthetic primer

<400> SEQUENCE: 70
attcccccgg atatgaggc                                               19

<210> SEQ ID NO 71
<211> LENGTH: 20
<212> TYPE: DNA
<213> ORGANISM: Artificial Sequence
<220> FEATURE:
<223> OTHER INFORMATION: Synthetic primer

<400> SEQUENCE: 71
ccgagcgtgg ctacagcttc                                              20

<210> SEQ ID NO 72
<211> LENGTH: 20
<212> TYPE: DNA
<213> ORGANISM: Artificial Sequence
<220> FEATURE:
<223> OTHER INFORMATION: Synthetic primer

<400> SEQUENCE: 72
acctggccgt caggcagctc                                              20

<210> SEQ ID NO 73
<211> LENGTH: 30
<212> TYPE: DNA
<213> ORGANISM: Artificial Sequence
<220> FEATURE:
<223> OTHER INFORMATION: Synthetic primer
```

```
<400> SEQUENCE: 73
ttgttggtat ggagtatagg ttgttgttat                                            30

<210> SEQ ID NO 74
<211> LENGTH: 28
<212> TYPE: DNA
<213> ORGANISM: Artificial Sequence
<220> FEATURE:
<223> OTHER INFORMATION: Synthetic primer

<400> SEQUENCE: 74
cctaccttcc tctacccata cttaaact                                              28
```